United States Patent
Tamano et al.

(10) Patent No.: US 9,782,199 B2
(45) Date of Patent: Oct. 10, 2017

(54) PUNCTURE DEVICE

(71) Applicants: MITSUBISHI PENCIL COMPANY, LIMITED, Tokyo (JP); TERUMO KABUSHIKI KAISHA, Tokyo (JP)

(72) Inventors: Hisami Tamano, Fujioka (JP); Satoru Sumiyoshi, Fujioka (JP); Atsushi Nakashima, Fujioka (JP); Yuusuke Kyogoku, Fujioka (JP)

(73) Assignees: MITSUBISHI PENCIL COMPANY, LIMITED, Tokyo (JP); TERUMO KABUSHIKI KAISHA, Tokyo (JP)

( * ) Notice: Subject to any disclaimer, the term of this patent is extended or adjusted under 35 U.S.C. 154(b) by 400 days.

(21) Appl. No.: 14/384,276

(22) PCT Filed: Mar. 22, 2013

(86) PCT No.: PCT/JP2013/058243
§ 371 (c)(1),
(2) Date: Sep. 10, 2014

(87) PCT Pub. No.: WO2013/141347
PCT Pub. Date: Sep. 26, 2013

(65) Prior Publication Data
US 2015/0039009 A1    Feb. 5, 2015

(30) Foreign Application Priority Data

Mar. 23, 2012 (JP) ................................. 2012-067144
Oct. 2, 2012 (JP) ................................. 2012-220072
(Continued)

(51) Int. Cl.
*A61B 17/34* (2006.01)
*A61M 25/06* (2006.01)

(52) U.S. Cl.
CPC ..... *A61B 17/3417* (2013.01); *A61M 25/0631* (2013.01)

(58) Field of Classification Search
CPC ...................... A61B 17/3417; A61M 25/0631
See application file for complete search history.

(56) References Cited

U.S. PATENT DOCUMENTS 5,772,636 A    6/1998  Brimhall et al.
5,772,643 A    6/1998  Howell et al.
(Continued)

FOREIGN PATENT DOCUMENTS

CN      1184677       6/1998
JP      9-234250 A    9/1997
(Continued)

OTHER PUBLICATIONS

International Search Report dated May 28, 2013, issued in corresponding application No. PCT/JP2013/058243.
(Continued)

*Primary Examiner* — Julian W Woo
(74) *Attorney, Agent, or Firm* — Westerman, Hattori, Daniels & Adrian, LLP

(57) ABSTRACT

To provide a puncture device which prevents components constituting a puncture device from being damaged by buckling (bending) etc., secures safety, and can be handled by a weak user easily. A puncture device is provided with an outer needle, an outer needle hub for retaining a base portion of the outer needle, an inner needle whose tip portion is inserted in the outer needle, an inner needle hub for retaining a base portion of the inner needle, an outer pipe fitted inside the inner needle hub so as to be moveable to and fro, and an inner pipe having a gripping device for gripping the outer
(Continued)

needle hub and fitted inside the outer pipe so as to be moveable to and fro, and at least the outer pipe is formed of a soft synthetic resin.

10 Claims, 40 Drawing Sheets

(30) Foreign Application Priority Data

| | | |
|---|---|---|
| Oct. 2, 2012 | (JP) | 2012-220073 |
| Mar. 19, 2013 | (JP) | 2013-056567 |
| Mar. 19, 2013 | (JP) | 2013-056568 |

(56) References Cited

U.S. PATENT DOCUMENTS

| | | | | |
|---|---|---|---|---|
| 6,638,254 B2* | 10/2003 | Nakagami | ......... | A61M 25/0631 604/164.01 |
| 6,872,193 B2* | 3/2005 | Shaw | ......... | A61M 25/0631 604/110 |
| 7,632,243 B2* | 12/2009 | Bialecki | ......... | A61M 25/0618 604/110 |
| 7,988,678 B2* | 8/2011 | Monson | ......... | A61M 5/344 604/200 |

FOREIGN PATENT DOCUMENTS

| | | |
|---|---|---|
| JP | 10-165511 A | 6/1998 |
| JP | 2000-501960 A | 2/2000 |
| JP | 2002-727 A | 1/2002 |
| JP | 2007-143876 A | 6/2007 |
| WO | 97/21458 A1 | 6/1997 |

OTHER PUBLICATIONS

Office Action dated Feb. 3, 2016, issued in counterpart Chinese Patent Application No. 201380016113A, with English translation. (10 pages).

* cited by examiner

Fig. 6
(a)
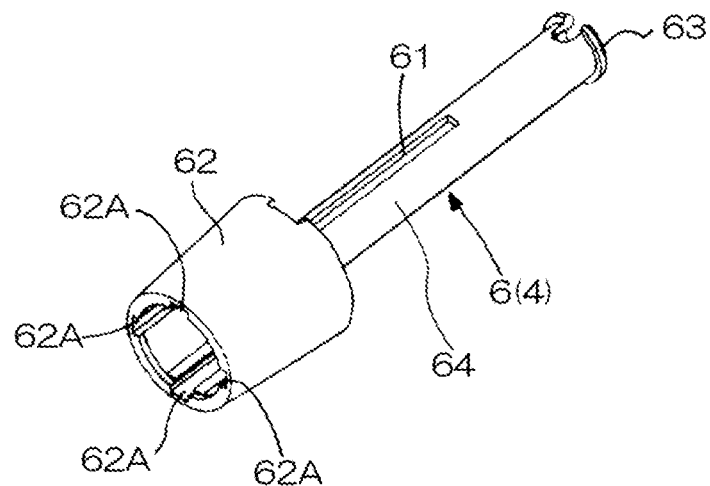
(b)
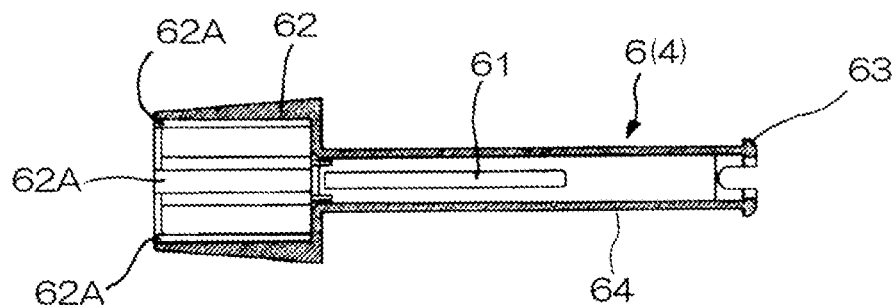
(c)
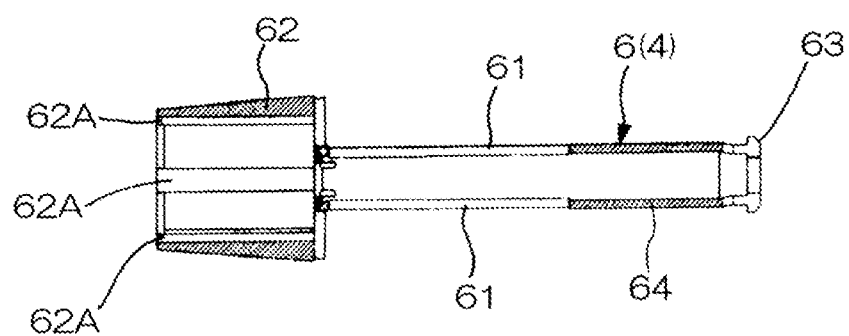

Fig. 16
(a)
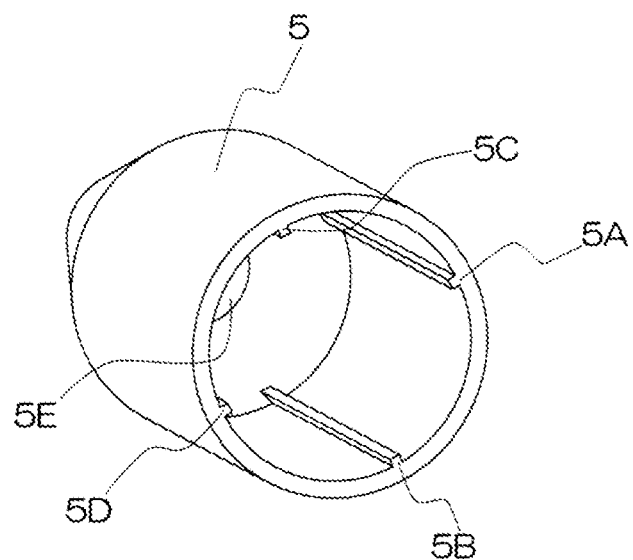
(b)
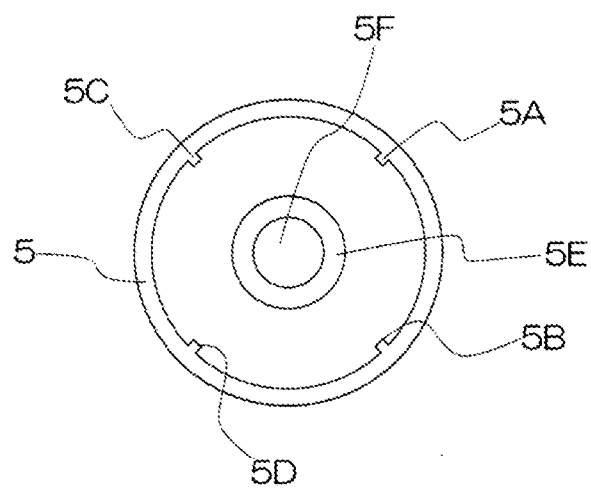

PUNCTURE DEVICE

TECHNICAL FIELD

The present invention relates to a puncture device, and more particularly to a puncture device for indwelling an outer needle (catheter) in a blood vessel.

BACKGROUND ART

Conventionally, a puncture device for indwelling an outer needle (catheter) in a blood vessel is known as disclosed in Patent Documents 1 and 2, for example.

Such a puncture device is provided with an outer needle, an outer needle hub for retaining the outer needle, an inner needle whose tip portion is inserted in the outer needle, and a cylindrical inner needle hub for retaining therein a base portion of the inner needle.

In particular, the puncture device disclosed in Patent Document 1 will be described with reference to FIG. 50.

As shown in FIG. 50(A), this puncture device 100 is provided with an outer needle 102a, an outer needle hub 102b, an inner needle 103 whose tip portion is inserted in the outer needle 102a, and a cylindrical inner needle hub 101 for retaining therein a base portion of the inner needle 103.

Further, the use of the puncture device 100 will be described. As shown in FIG. 50(A), in a situation where a slide cover 104 is accommodated in the inner needle hub 101 and a tip 103a of the inner needle 103 has projected from a tip of the outer needle 102a, a puncture (paracentesis) is carried out on a patient's body 110.

Then, after moving the outer needle 102a into the body (see FIG. 50(B)), in a situation where the outer needle 102a is indwelled in the body, when the inner needle hub 101 is pulled towards the user, the slide cover 104 is extended and the tip 103a of the inner needle comes out of the body (see FIG. 50(C)).

By further pulling the inner needle hub 101 in the same direction, the tip 103a of the inner needle 103 is retained in the slide cover 104, without contacting a hand.

Subsequently, in such a situation, the inner needle hub 101 is rotated in a circumferential direction (see FIG. 50(D)), the whole slide cover 104 rotates in the same direction, and the holder 105 at the tip side is released (removed).

As a result, only the outer needle 102a is indwelled inside the body, and the inner needle hub 101 in which the inner needle 103 is accommodated can be removed, and the inner needle 103 can be discarded as it is (see FIG. 50(E)).

Further, the puncture device disclosed in Patent Document 2 is arranged such that, although not shown, in a situation where the outer needle is indwelled inside the body, by pushing a push piece provided for the inner needle hub, the inner needle can be accommodated inside the inner needle hub without touching the inner needle.

PRIOR ART DOCUMENTS

Patent Documents

Patent Document 1: Japanese Patent Application Publication No. 2002-000727

Patent Document 2; Japanese Patent Application Publication No. 2007-143876

SUMMARY OF THE INVENTION

Problems to be Solved by the Invention

Incidentally, in the puncture device disclosed in Patent Document 2 above, there is a technical problem that if a worker forgets to push the push piece, the inner needle is discarded in a situation where it is not accommodated in the inner needle hub, thus being very dangerous for the worker, and there is a possibility that safety may not be secured.

On the other hand, in the puncture device disclosed in Patent Document 1 above, the inner needle can be accommodated in the inner needle hub in a situation where the outer needle is indwelled inside the body. Thus, it is possible to work safely.

However, in the puncture device disclosed in Patent Document 1, at the time of pulling the inner needle out of the outer needle, when the direction to pull the inner needle hub is an inclined direction (which is not on an extension of an axis of the inner needle), bending force is applied to the inner needle hub 101, the slide cover 104, etc., so that the inner needle hub 101, the slide cover 104, etc. may be buckled (bent), leading to possible damages. Further, if the inner needle hub 101, the slide cover 104, etc. are damaged, there is a possibility that the inner needle 3 may come out of the slide cover 104 etc., leading to a technical problem that it is very dangerous for the worker, and there is a possibility that safety may not be secured.

Furthermore, there is a technical problem that since the slide cover 104 slides inside the inner needle hub 101, its slide resistance is large and the handling is not easy for the weak user.

The present invention has been made in order to solve the above-mentioned technical problems, and aims to provide a puncture device which prevents components constituting the puncture device from being damaged by buckling (bending) etc., secures safety, and allows a weak user to handle it easily.

Means for Solving the Problems

The puncture device in accordance with the present invention made in order to solve the above-mentioned technical problems is a puncture device provided with an outer needle, an outer needle hub for retaining a base portion of the above-mentioned outer needle, an inner needle whose tip portion is inserted in the above-mentioned outer needle, an inner needle hub for retaining a base portion of the above-mentioned inner needle, an outer pipe fitted inside the inner needle hub so as to be moveable to and fro, and an inner pipe having a gripping means for gripping the above-mentioned outer needle hub and fitted inside the above-mentioned outer pipe so as to be moveable to and fro, wherein at least the above-mentioned outer pipe is formed of a soft synthetic resin material.

As such, at least the outer pipe is formed of a soft synthetic resin material, and the outer pipe is bent by the above-mentioned bending force, but the damages, such as a crack etc. can be prevented. Further, as a result of preventing damages etc. of the outer pipe, there is no possibility of the outer pipe being separated from the inner needle hub and the inner needle being exposed, and it is possible to secure safety.

Here, it is desirable that the above-mentioned inner pipe is formed of a soft synthetic resin material. When the inner pipe is thus formed of a soft synthetic resin material, it is possible to prevent the damage, such as a crack, of the inner pipe caused by the above-mentioned bending force.

Further, it is desirable that the above-mentioned inner needle hub is formed of a soft synthetic resin material. When the inner needle hub is thus formed of a soft synthetic resin material, it is possible to prevent the damage, such as a crack, of the inner needle hub caused by the above-mentioned bending force.

In addition, it is desirable that the above-mentioned soft synthetic resin material is a synthetic resin whose elongation percentage is 100% or more. Furthermore, it is desirable that the above-mentioned soft synthetic resin material is polypropylene.

As described above, in the case where the inner pipe, the outer pipe, and the inner needle hub are formed of polypropylene, the slide resistance can be reduced, so that operation of withdrawing the inner needle hub can be performed with less power. Thus, even a weak user can handle it easily.

Effects of the Invention

According to the present invention, a puncture device can be obtained which prevents components constituting the puncture device from being damaged by buckling (bending) etc., secures safety, and can be handled by a weak user easily.

BRIEF DESCRIPTION OF THE DRAWINGS

FIG. 6 are views showing an outer pipe, in which FIG. 6(a) is a perspective view, FIG. 6(b) is a longitudinal sectional view, and FIG. 6(c) is a longitudinal sectional view whose section is different from that of the longitudinal sectional view of FIG. 6(b) by 90 degrees in a circumferential direction.

FIG. 8 are views showing the inner pipe in an unfolded configuration, in which FIG. 8(a) is a plan view and FIG. 8(b) is a sectional view along the line A-A of FIG. 8(a).

FIG. 9 are views showing a puncture state for explaining a procedure which uses the puncture device shown in FIG. 1 in which FIG. 9(a) is a longitudinal sectional view, and FIG. 9(b) is a longitudinal sectional view whose section is different from that of the longitudinal sectional view of FIG. 9(a) by 90 degrees in a circumferential direction.

FIG. 10 are views showing a situation where the inner needle hub is expanded, for explaining the procedure which uses the puncture device shown in FIG. 1, in which FIG. 10(a) is a longitudinal sectional view and FIG. 10(b) is a longitudinal sectional view whose section is different from that of the longitudinal sectional view of FIG. 10(a) by 90 degrees in a circumferential direction.

FIG. 11 are views showing a situation where the expansion of the inner needle hub is completed, for explaining the procedure which uses the puncture device shown in FIG. 1, in which FIG. 11(a) is a longitudinal sectional view and FIG. 11(b) is a longitudinal sectional view whose section is different from that of the longitudinal sectional view of FIG. 11(a) by 90 degrees in a circumferential direction.

FIG. 12 are views showing a situation where an outer needle is indwelled, for explaining the procedure which uses the puncture device shown in FIG. 1, in which FIG. 12(a) is a longitudinal sectional view and FIG. 12(b) is a longitudinal sectional view whose section is different from that of the longitudinal sectional view of FIG. 12(a) by 90 degrees in a circumferential direction.

FIG. 16 are views of the protector shown in FIG. 15, in which FIG. 16(a) is a perspective view and FIG. 16(b) is a plan view from an inner needle hub inserting side.

FIG. 29 are views illustrating the puncture device shown in FIG. 25, in which FIG. 29(a) is a longitudinal sectional view and FIG. 29(b) is a longitudinal sectional view whose section is different from that of the longitudinal sectional view of FIG. 29(a) by 90 degrees in a circumferential direction.

FIG. 30 are views illustrating the inner needle hub of the puncture device shown in FIG. 25, in which FIG. 30(a) is a side view and FIG. 30(b) is a longitudinal sectional view.

FIG. 35 are views of the puncture device for explaining the procedure which mounts the protector, in which FIG. 35(a) is a side view and FIG. 35(b) is a longitudinal sectional view.

EXPLANATION OF REFERENCE SIGNS

Figure 1:
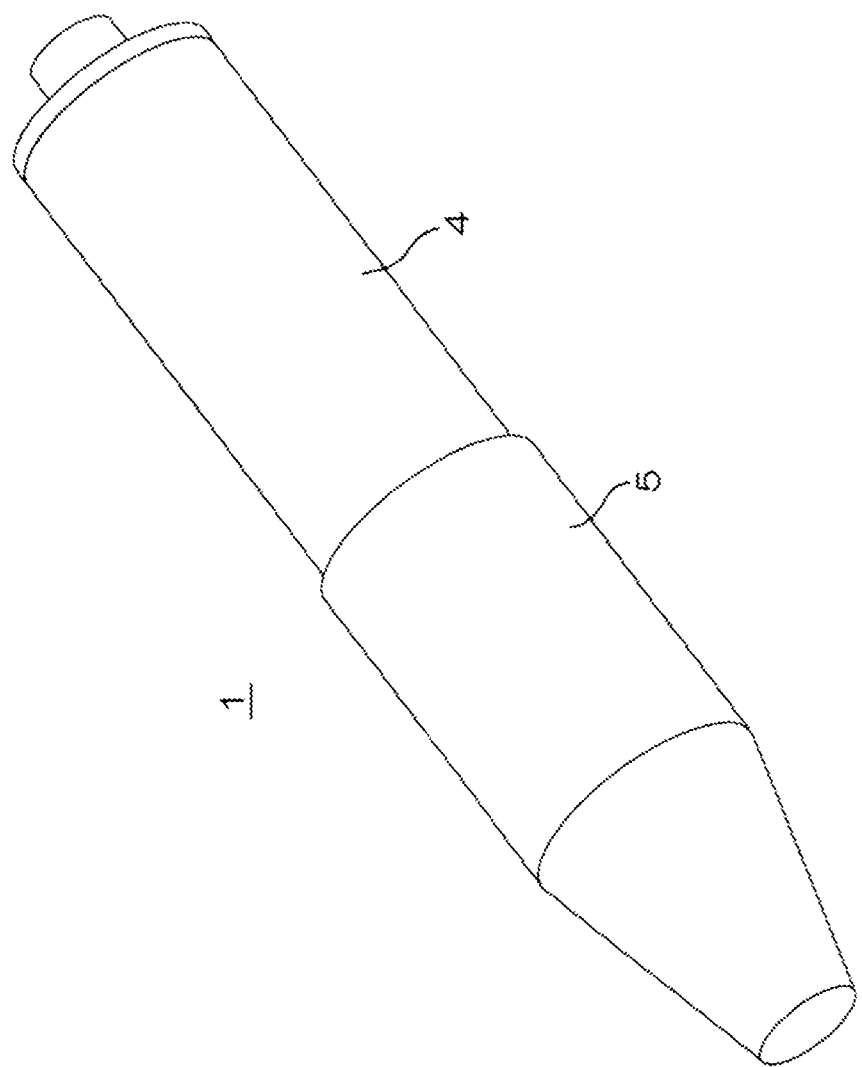
FIG. 1 is a perspective view showing an appearance of a puncture device in accordance with a first preferred embodiment of the present invention.

1: puncture device
2: catheter
21: outer needle
22: outer needle hub
22A: wings (projection parts)
22B: branch pipe
22C: step portion
3: inner needle
4: syringe
5: protector
5A-5D: contact portions
5E: outer needle hub supporting portion
5a: outer needle hub supporting portion
5b: main body
5c1: opening (undersurface side)
5c2: opening (cylinder part opposite end side)
5d: rib-like frame
5d1: rib-like frame extension
5e: locked projection
5f: contact portion
5g: contact portion
5h: guided part
5i: guided part
6: outer pipe (cylindrical member)
7: inner pipe (cylindrical member)
7A: lower part
7B: upper part
41: inner needle hub
41A: main body
41a: end portion
41b: fitting portion
41b1: locking hole
41c: opening
41d: through hole
41e: rib-like projection
41f: bracing projection
41g: rib-like projection
41h: protrusion
42: plug
42a: needle retaining part
51: outer needle hub supporting portion
52: supporting leg
52c: locking member
53: opening
61: slit
62: arm opening/closing part (gripping means)
71: head part
71A: arm (gripping means)
72: shaft
72A: projection
72B: standing piece
73: through hole
73A, 73B: grooves
110: patient's body

MODE FOR CARRYING OUT THE INVENTION

First Preferred Embodiment

Hereinafter, a puncture device in accordance with a first preferred embodiment of the present invention will be described with reference to FIGS. 1 to 12.

Figure 2:
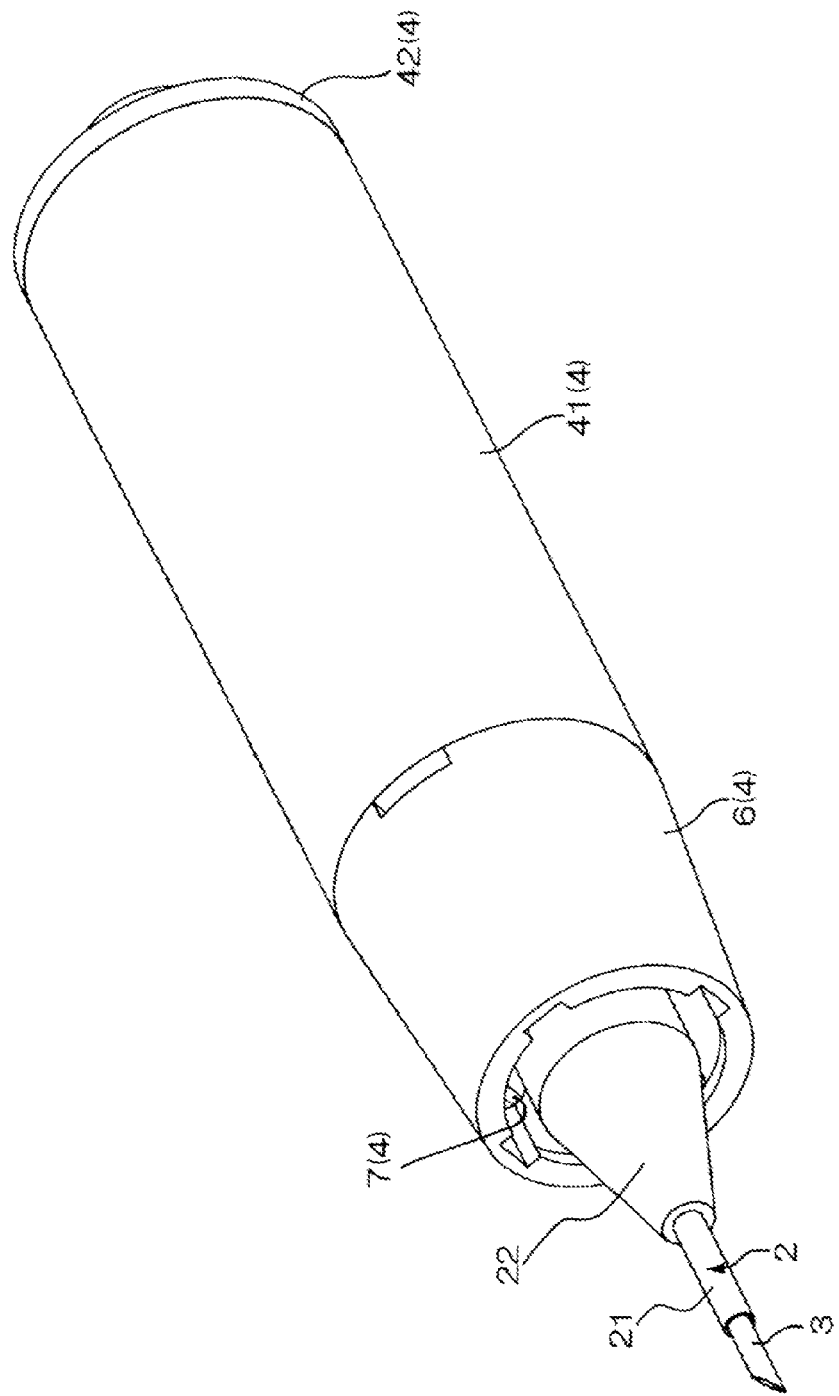
FIG. 2 is a perspective view showing a situation where a protector of the puncture device in FIG. 1 is removed.

As shown in FIGS. 1 and 2, a puncture device 1 is provided with an outer needle 21, an inner needle 3 whose tip portion (left-hand side) is inserted in the above-mentioned outer needle 21, a cylindrical syringe 4 for retaining an end portion (base portion) of the above-mentioned inner needle 3, and a protector 5 which covers the above-mentioned outer needle 21, and the above-mentioned inner needle 3. Further, in the above-mentioned puncture device 1, all the components except the above-mentioned inner needle 3 are made of resin. It should be noted that the above-mentioned outer needle 21 and the above-mentioned inner needle 3 cannot be seen in FIG. 1, since they are covered with the above-mentioned protector 5.

Figure 3:
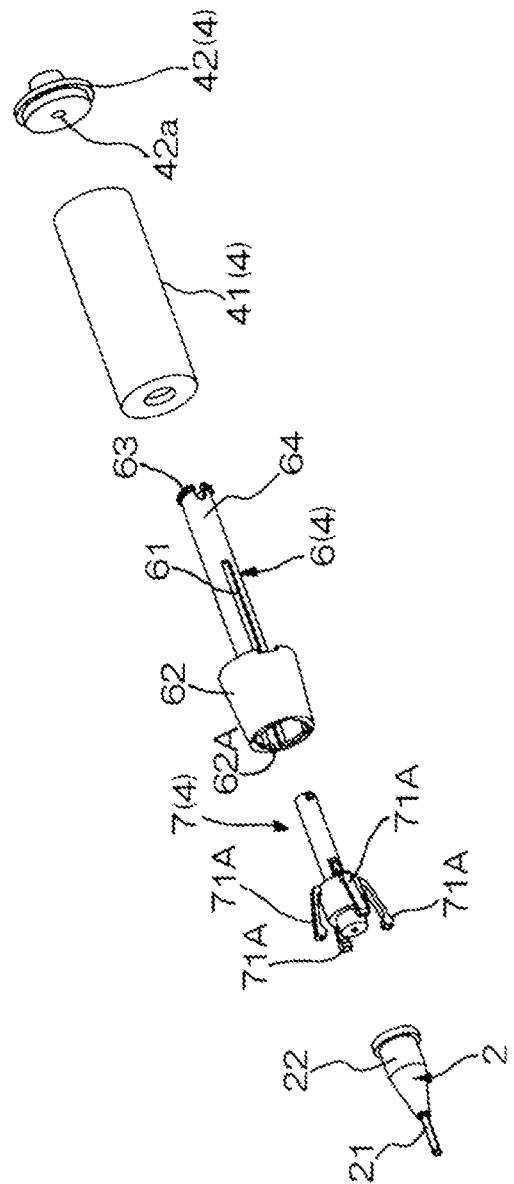
FIG. 3 is an exploded perspective view except the protector of the puncture device in FIG. 1.

Further, as shown in FIGS. 2 and 3, the above-mentioned catheter 2 has the outer needle 21 formed of a flexible hollow pipe and the outer needle hub 22 for retaining the base portion of the outer needle 21.

As shown in FIGS. 2 to 5, the above-mentioned syringe 4 is provided with a cylindrical inner needle hub 41 and a plug 42 which is press fitted into and attached to a base portion (right-hand side) of the above-mentioned inner needle hub 41 and has a substantially cylindrical needle retaining part 42a by which the base portion of the above-mentioned inner needle 3 is retained.

Further, the above-mentioned syringe 4 is provided with an outer pipe 6 fitted inside the above-mentioned inner needle hub 41 so as to be moveable to and fro, and an inner pipe 7 having four arms 71A for gripping the above-mentioned outer needle hub and fitted inside the above-mentioned outer pipe 6 so as to be moveable to and fro.

It should be noted that although this preferred embodiment shows a situation where the four above-mentioned arms 71A are formed at the above-mentioned inner pipe 7, the outer needle hub 22 may only be retained by a plurality of arms.

As shown in FIG. 6, the above-mentioned outer pipe 6 is provided with a slit 61 formed along an axis of a shaft 64 of the above-mentioned outer pipe 6 (formed along a direction of back and forth movement of the inner pipe 7) and an arm opening/closing part 62 which accommodates the four above-mentioned arms 71A, and cylindrically formed as a whole.

It should be noted that the four above-mentioned arms 71A are arranged to be moveable to and fro and guided by guide grooves 62A formed at both sides on the inner surface of the above-mentioned arm opening/closing part 62.

Figure 5:
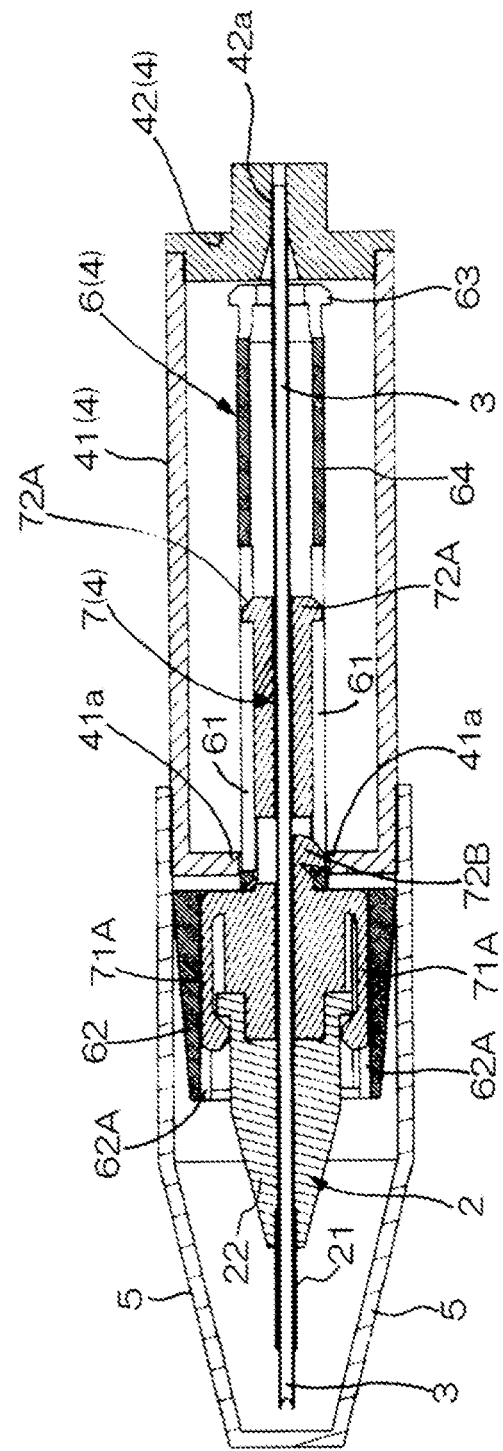
FIG. 5 is a longitudinal sectional view showing the puncture device of FIG. 1, and is a longitudinal sectional view whose section is different from that of the longitudinal sectional view of FIG. 4 by 90 degrees in a circumferential direction.

As shown in FIG. 5 and FIG. 6(c), the above-mentioned slits 61 are axisymmetrically formed at two places, an upper part and a lower part in the periphery of the above-mentioned outer pipe 6.

Figure 4:
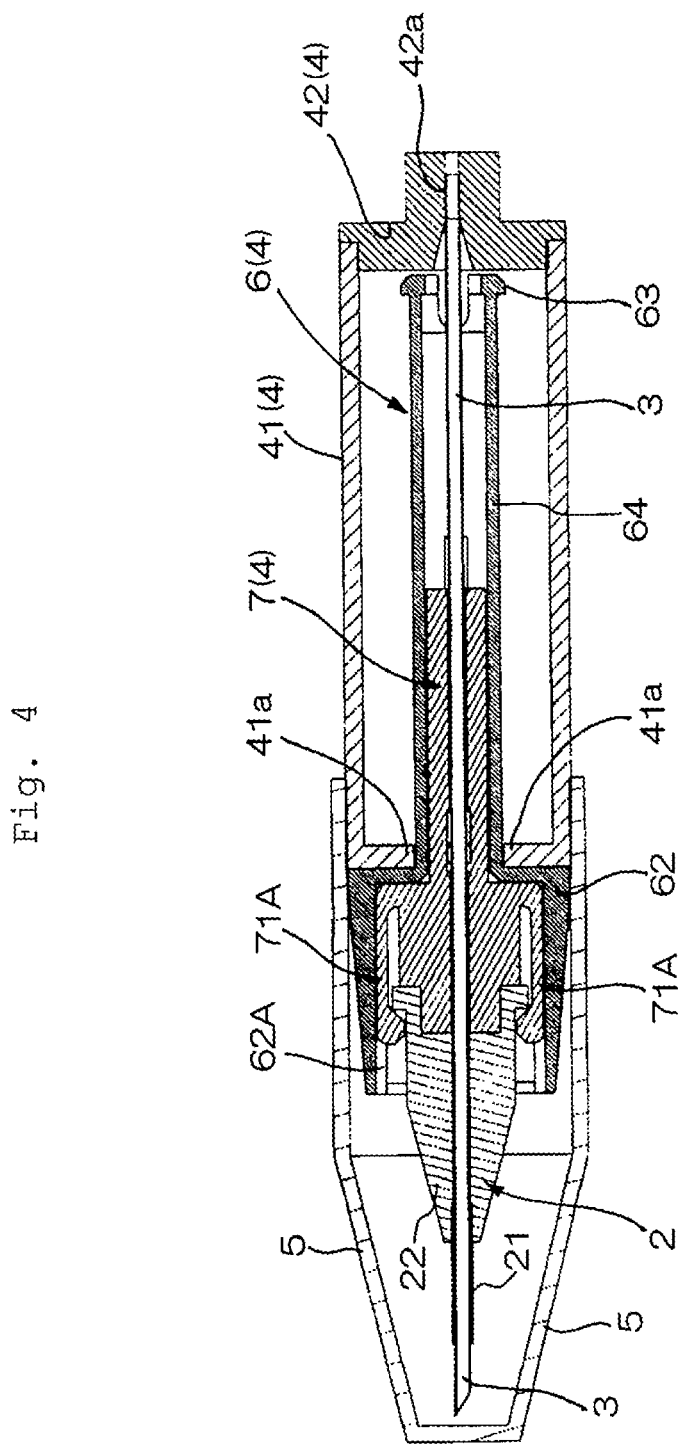
FIG. 4 is a longitudinal sectional view showing the puncture device shown in FIG. 1.

Further, as shown in FIGS. 4 and 5, when the above-mentioned inner pipe 7 is accommodated in the above-mentioned outer pipe 6, the four above-mentioned arms 71A are folded, and the above-mentioned arm opening/closing part 62 grasps the above-mentioned outer needle hub 22.

Figure 11:
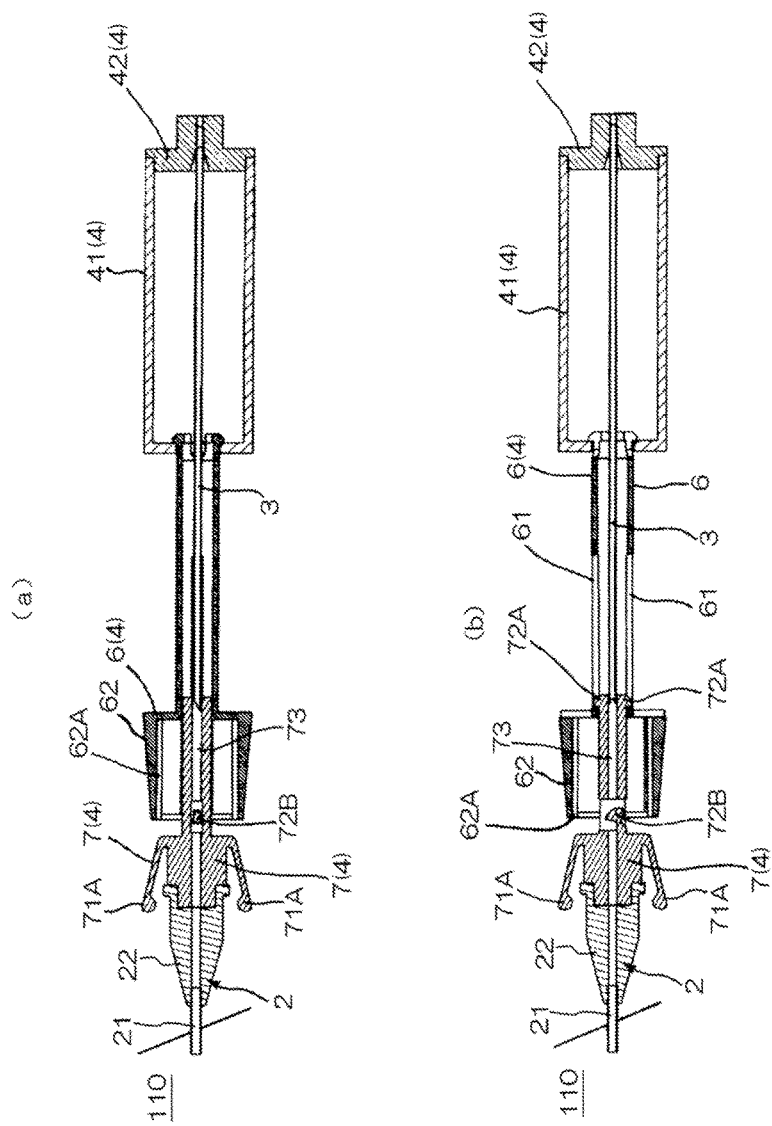
Figure 12:
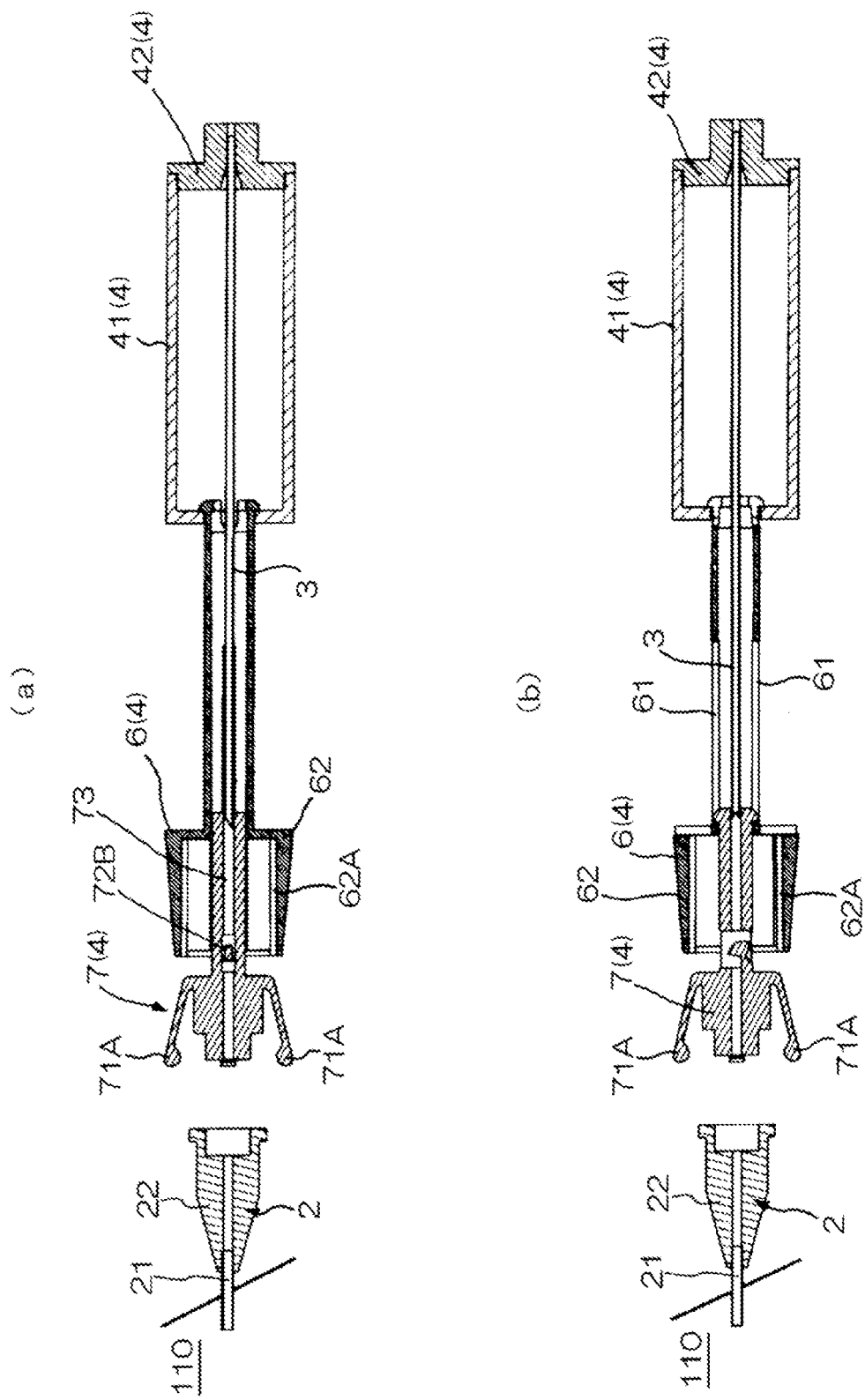

On the other hand, when the above-mentioned inner pipe 7 is pulled (advanced) from the above-mentioned outer pipe 6, the restriction by the guide grooves 62A (arm opening/closing part 62) is released as shown in FIGS. 11 and 12 so that the four above-mentioned arms 71A are unfolded by elasticity of the arm 71A itself to release the above-mentioned outer needle hub 22.

As described above, a gripping means for gripping the above-mentioned outer needle hub 22 is constituted by the four above-mentioned arms 71A and the above-mentioned arm opening/closing part 62. In a situation where the four above-mentioned arms 71A are retracted into the arm opening/closing part 62, the outer needle hub 22 is grasped as shown in FIGS. 4 and 5. In a situation where the four above-mentioned arms 71A are advanced from the arm opening/closing part 62, the outer needle hub 22 is released as shown in FIGS. 11 and 12.

In particular, the four above-mentioned arms 71A are formed in advance to have an unfolded shape with respect to the periphery of the inner pipe 7 as shown in FIG. 3.

Further, in the case where the arms 71A of the above-mentioned inner pipe 7 are inserted (accommodated) in the guide grooves 62A (see FIG. 6) of the above-mentioned outer pipe 6, the four above-mentioned arms 71A are folded by the above-mentioned arm opening/closing part 62. That is to say, the above-mentioned arm opening/closing part 62 folds the four above-mentioned arms 71A so as to cause the four above-mentioned arms 71A to grasp the above-mentioned outer needle hub 22.

Furthermore, as the above-mentioned inner pipe 7 is pulled (advanced) from the above-mentioned outer pipe 6, the four above-mentioned arms 71A are pulled out of the above-mentioned arm opening/closing part 62 and return to the originally unfolded state as shown in FIGS. 11 and 12. That is to say, the above-mentioned arm opening/closing part 62 causes the four above-mentioned arms 71A to be in the open state, and the four above-mentioned arms 71A allows the above-mentioned catheter 2 to be released.

Figure 7:
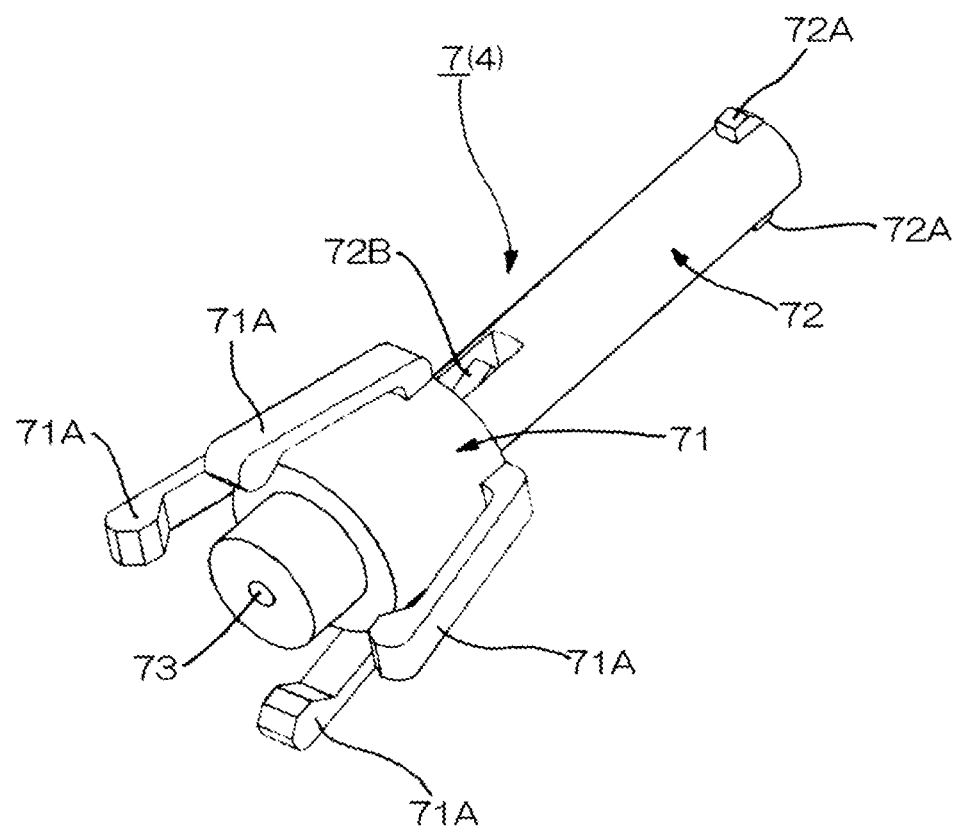
FIG. 7 is the perspective view showing an inner pipe.

As shown in FIG. 7, the above-mentioned inner pipe 7 has ahead part 71 provided with the four above-mentioned arms 71A, a shaft 72 having a diameter smaller than that of the above-mentioned head part 71, and a through hole 73 which penetrates the centers of the above-mentioned head part 71 and the above-mentioned shaft 72, and through which the above-mentioned inner needle 3 is inserted, thus being cylindrically formed as a whole.

The above-mentioned shaft 72 is provided with a projection 72A which is moveably accommodated in the above-mentioned slit 61 of the above-mentioned outer pipe 6, and a standing piece 72B which is pushed out to stand by the inner needle 3 in the above-mentioned through hole 73 and engaged with the above-mentioned slit 61.

The above-mentioned projections 72A are formed axisymmetrically at two places, an upper surface and an under surface of the above-mentioned shaft 72, so as to respectively correspond to the above-mentioned slits 61 (see FIG. 5). Further, the above-mentioned slit 61 and the above-mentioned projection 72A restrict the back and forth movement of the above-mentioned inner pipe 7 with respect to the above-mentioned outer pipe 6 (back and forth movement of the above-mentioned outer pipe 6 with respect to the inner pipe 7).

It should be noted that when the above-mentioned inner pipe 7 is caused to advance relatively to the above-mentioned outer pipe 6, the above-mentioned projection 72A is arranged to be caught by an end portion of the slit 61, so as not to separate the above-mentioned outer pipe 6 from the inner pipe 7.

Figure 8:
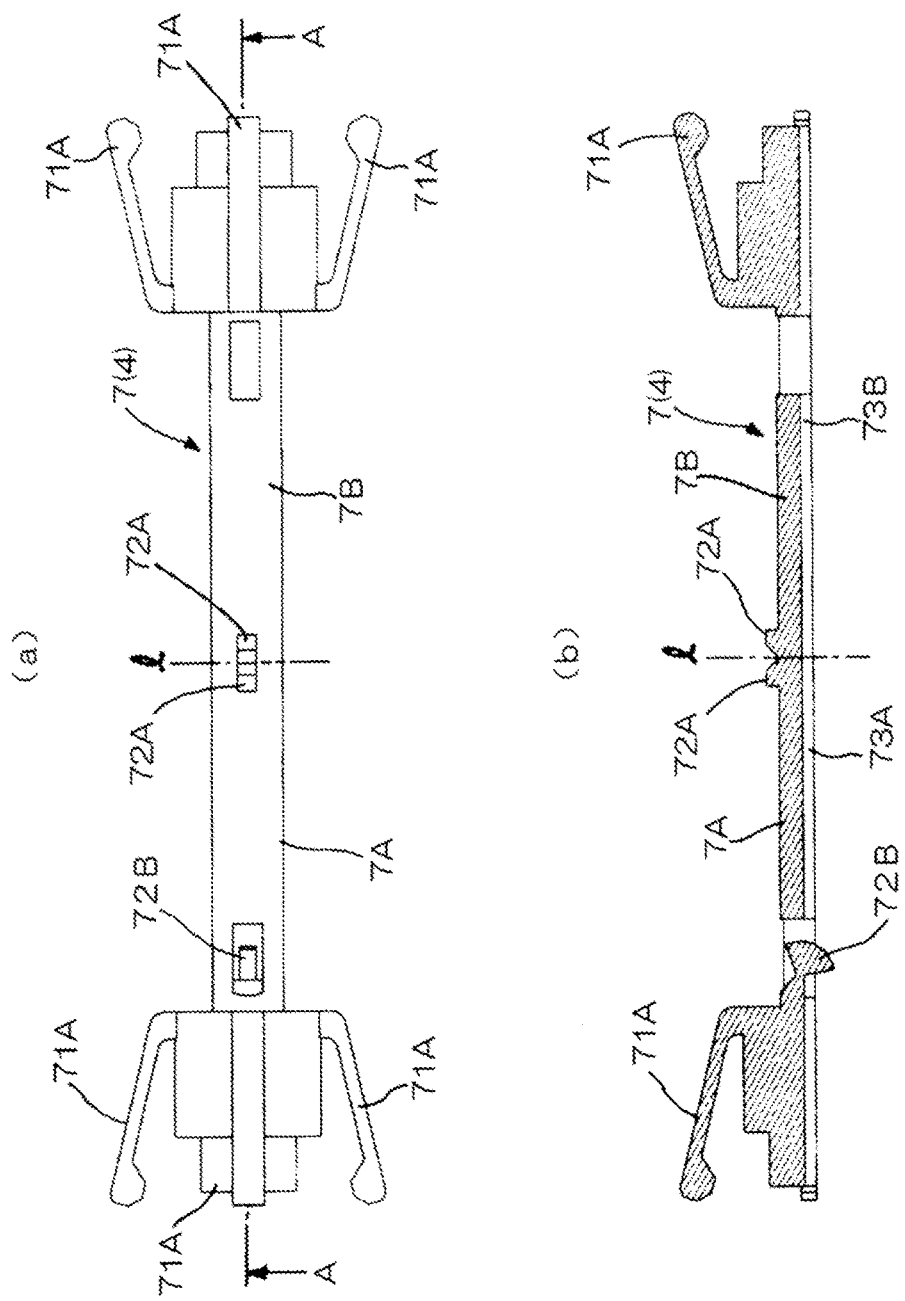

Here, as shown in FIG. 8, the above-mentioned inner pipe 7 is a component comprising the lower part 7A (left-hand side) provided with the above-mentioned standing piece 72B and the upper part 7B (right-hand side) which are on opposite sides of a central line 1 and integrally formed. It is formed by folding the above-mentioned lower part 7A and the above-mentioned upper part 7B along a score line (central line 1).

Further, grooves 73A and 73B whose cross sections are in the shape of a semicircle are formed along the axial direction of the above-mentioned inner pipe 7 in the centers of the above-mentioned lower part 7A and the above-mentioned upper part 7B, respectively. When the above-mentioned lower part 7A and the above-mentioned upper part 7B are folded, these grooves 73A and 73B form one through hole 73.

Furthermore, as shown in FIG. 5, as the above-mentioned inner needle 3 is inserted (accommodated) in the above-mentioned through hole 73, the above-mentioned standing piece 72B is pushed out to stand up by the periphery of the above-mentioned inner needle 3 and engages with an end portion of the above-mentioned slit 61.

Here, the above-mentioned standing piece 72B engages with the end portion on the above-mentioned catheter 2 side of the above-mentioned slit 61, and therefore sandwiches the above-mentioned outer pipe 6 in conjunction with the above-mentioned head part 71 of the above-mentioned inner pipe 7, thus being caught by the above-mentioned outer pipe 6.

In other words, in the case where the inner needle 3 is in the above-mentioned through hole 73, the above-mentioned inner needle 3 allows the above-mentioned standing piece 72B to stand up, the outer pipe 6 and the inner pipe 7 are unified, and the above-mentioned outer pipe 6 is inhibited from being pulled out of the above-mentioned inner pipe 7.

Further, when the above-mentioned inner needle 3 is pulled from the inside of the above-mentioned through hole 73 and the above-mentioned standing piece 72B is not pushed out by the inner needle 3, it is accommodated within (returns to) the above-mentioned inner pipe 7 so as to close the above-mentioned through hole 73 and disengaged from the above-mentioned slit 61.

In other words, in the case where the inner needle 3 is not in the above-mentioned through hole 73, the above-mentioned standing piece 72B is not caught by the above-mentioned outer pipe 6, so that the outer pipe 6 and the inner pipe 7 may be separable and the above-mentioned inner pipe 7 can be pulled from the above-mentioned outer pipe 6.

It should be noted that engaging portions are respectively formed at end portions 41a and 63 of the above-mentioned inner needle hub 41 and the above-mentioned outer pipe 6 which are arranged so as not to be separated (spaced apart) from each other, since the engaging portions formed at the above-mentioned end portions 41a and 63 are fit together when they are expanded.

Next, a case where such a puncture device 1 is used will be described.

Firstly, the protector 5 is removed from the puncture device 1 shown in FIGS. 1 and 4, and the catheter 2 and the inner needle 3 are exposed as shown in FIG. 2. Further, as shown in FIG. 9, the above-mentioned outer needle 21 and the above-mentioned inner needle 3 puncture a blood vessel (patient's body 110).

Then, in order to indwell the above-mentioned outer needle 21, the above-mentioned inner needle hub 41 is moved along the axial direction and in a direction away from the above-mentioned outer needle 21 (pull-out operation is performed). The above-mentioned syringe 4 is expanded by pulling out this inner needle hub 41.

Figure 9:
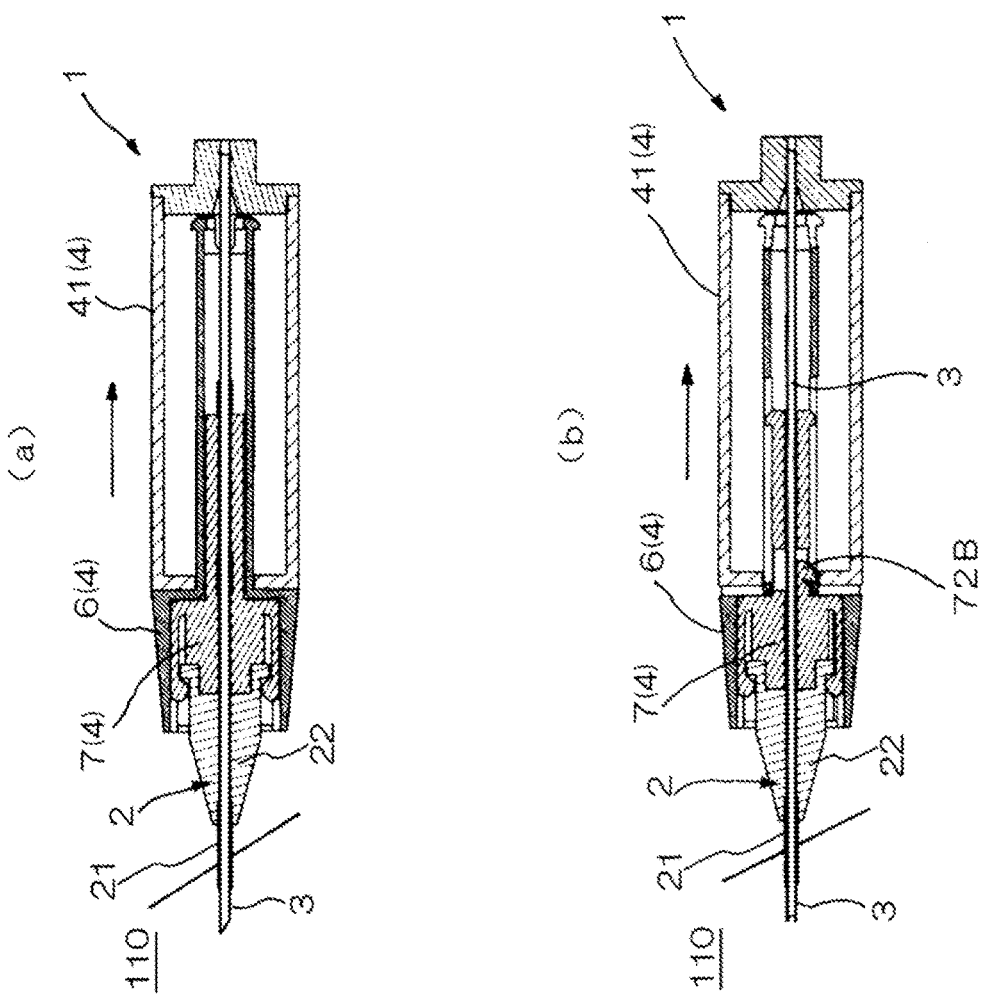
Figure 10:
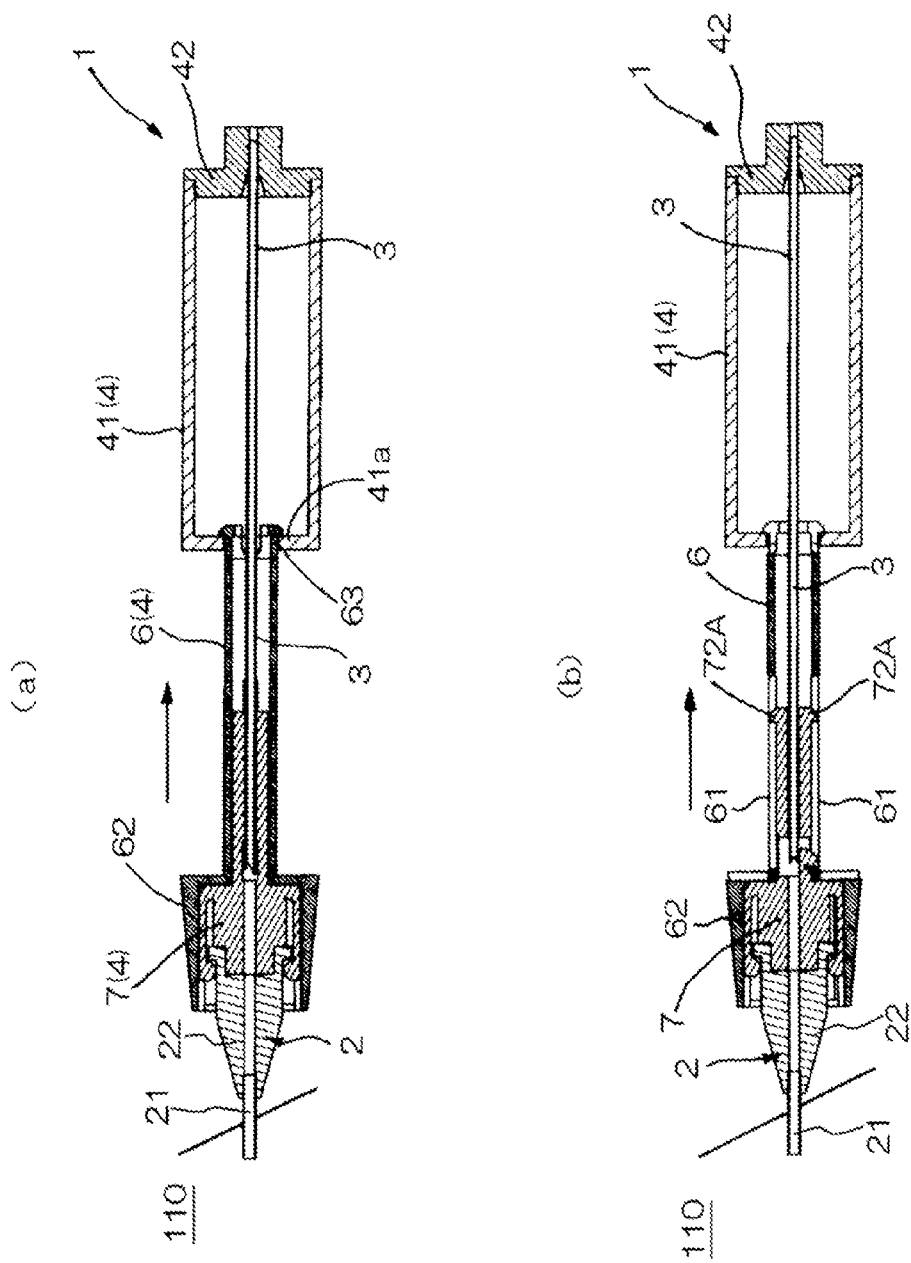

In particular, in a situation where the above-mentioned outer needle 21 is indwelled, when the above-mentioned inner needle hub 41 is moved along the axial direction away from the above-mentioned outer needle 21 (pull-out operation is performed in the direction of the arrows shown in FIG. 9), the above-mentioned inner needle hub 41 moves along the axial direction, and the above-mentioned syringe 4 is expanded as a whole. At this time, the outer needle hub 22 is retained by the inner pipe 7, and the standing piece 72B unifies the inner pipe 7 with the outer pipe 6.

Therefore, as the inner needle hub 41 for retaining the rear end portion (base portion) of the inner needle 3 is moved along the axial direction, the inner needle 3 similarly moves along the axial direction. Further, the inner needle 3 is pulled from the outer needle 21, and the thus pulled inner needle 3 is covered with the inner pipe 7, the outer pipe 6, and the inner needle hub 41 (see FIG. 10).

The above-mentioned inner needle hub 41 is further moved away from the above-mentioned outer needle 21 along the axial direction. Then, when the tip of the inner needle 3 passes by the standing piece 72B as shown in FIG. 11, the force is not applied to the standing piece 72B from the side of the above-mentioned inner needle 3, and it returns to the original state and closes the through hole 73.

As such, even if the force of moving the inner needle hub 41 is applied to the catheter 2 side, the above-mentioned standing piece 72B inhibits the movement of the inner needle 3, which does not return into the outer needle 21 again.

Furthermore, when protrusion of the standing piece 72B by the above-mentioned inner needle 3 is cancelled, the above-mentioned outer pipe 6 is disengaged. As a result, the outer pipe 6 and the inner pipe 7 become separable, and it follows that as the above-mentioned inner needle hub 41 moves, the above-mentioned outer pipe 6 moves along the axial direction.

At this time, since the above-mentioned slit 61 is guided by the above-mentioned projection 72A, the above-mentioned outer pipe 6 is pulled from the above-mentioned inner needle hub 41, whilst being guided by the projection 72A of the above-mentioned inner pipe 7.

Further, when the above-mentioned inner needle hub 41 is moved away from the above-mentioned outer needle 21 along the axial direction, the above-mentioned outer pipe 6 is moved, and the above-mentioned inner pipe 7 is pulled from the above-mentioned outer pipe 6, then the four above-mentioned arms 71A are opened as shown in FIG. 11, and the retention of the outer needle hub 22 by the four above-mentioned arms 71A is released.

That is to say, by separating the above-mentioned inner needle hub 41 from the above-mentioned outer needle 21 along the axial direction and expanding the above-mentioned syringe 4, the above-mentioned inner needle 3 pulled from the above-mentioned catheter 2 is accommodated inside the above-mentioned inner pipe 7, an outer pipe 6, and the inner needle hub 41, then the outer needle hub 22 is released from the state where the outer needle hub 22 is retained by the four above-mentioned arms 71A and arm opening/closing parts 62.

Accordingly, as shown in FIG. 12, whilst the above-mentioned catheter 2 (outer needle 21) indwelling in a blood vessel, the above-mentioned inner needle 3 is pulled from the above-mentioned outer needle 21 and accommodated inside the above-mentioned inner needle hub 4, and the above-mentioned outer needle hub 22 is removed from the above-mentioned syringe 4.

Thus, only by pulling the above-mentioned inner needle 3 from the above-mentioned outer needle 21, the above-mentioned puncture device 1 can accommodate the above-mentioned inner needle 3 in the above-mentioned inner needle hub 4, and the above-mentioned outer needle hub 22 can be removed from the above-mentioned inner needle hub 4.

It should be noted that although the first preferred embodiment has been described with reference to the case where the cylinder body is constituted by the above-mentioned outer pipe 6 and the above-mentioned inner pipe 7, the present invention is not particularly limited to this structure. For example, the puncture device may be provided with a relay pipe which relays the above-mentioned inner needle hub to the outer pipe and the inner pipe. The above-mentioned cylinder body may have a gripping means for gripping the catheter, and it may only be attached so as to be inserted (accommodated) in the inner needle hub and move back and forth.

Further, although the first preferred embodiment has been described with reference to the case where the gripping means is constituted by the four above-mentioned arms 71A and the above-mentioned arm opening/closing parts 62, the present invention is not particularly limited to this structure. The above-mentioned gripping means may only be arranged such that the outer needle hub can be released when the inner needle pulled from the outer needle is accommodated in the cylinder body by moving the inner needle hub away from the outer needle along the axial direction to expand the syringe.

As described above, the first above-mentioned preferred embodiment is characterized in that the puncture device provided with the outer needle, the outer needle hub for retaining the base portion of the above-mentioned outer needle, the inner needle whose tip portion is inserted in the above-mentioned outer needle, and the cylindrical syringe for retaining the base portion of the above-mentioned inner needle; the above-mentioned syringe is provided with the inner needle hub for retaining the base portion of the above-mentioned inner needle and the cylinder body which has the gripping means for gripping the above-mentioned outer needle hub and is mounted inside the above-mentioned inner needle hub to move back and forth; by moving the above-mentioned inner needle hub away from the above-mentioned outer needle along the axial direction to expand the above-mentioned syringe, the above-mentioned inner needle pulled from the above-mentioned outer needle is accommodated inside the above-mentioned inner needle hub or inside the inner needle hub and cylinder body, the above-mentioned gripping means releases the above-mentioned outer needle hub, and the above-mentioned outer needle hub is removed from the above-mentioned inner needle hub.

According to such a structure, the inner needle pulled from the outer needle is accommodated in the inner needle hub by moving (pulling) the inner needle hub away along the axial direction to expand the syringe. Further, the gripping means cancels (releases) the grip of the outer needle hub.

Therefore, since the outer needle hub can be removed from the inner needle hub by only pulling the inner needle from the outer needle, it is unlikely to cause pain to a patient and the smooth removal can be performed easily. Further, since the inner needle is reliably accommodated inside the inner needle hub, worker's safety can be secured.

Here, the above-mentioned cylinder body is provided with the outer pipe mounted inside the above-mentioned inner needle hub so as to be moveable to and fro, and the inner pipe which has a plurality of arms for gripping the above-mentioned outer needle hub and is mounted inside the above-mentioned outer pipe so as to be moveable to and fro; the above-mentioned outer pipe has the arm opening/closing part in which the plurality of above-mentioned arms are opened/closed as the above-mentioned inner pipe is accommodated inside the above-mentioned outer pipe or pulled from the inside of the above-mentioned outer pipe; the above-mentioned inner pipe is provided with the through hole into which the above-mentioned inner needle is inserted, the standing piece which is caused to be pushed out and stand by the above-mentioned inner needle in the above-mentioned through hole and caught by the outer pipe, and the plurality of arms which are opened/closed by the above-mentioned arm opening/closing part and grip the catheter; by moving the above-mentioned inner needle hub away from the above-mentioned outer needle along the axial direction and pulling out the above-mentioned inner needle, an engaging state of the outer pipe and inner pipe caused by the above-mentioned standing piece is canceled; the arm opening/closing part of the above-mentioned outer pipe is moved relatively to the inner pipe, and a plurality of arms which grip an outer needle hub are opened, whereby the above-mentioned outer needle hub is desirably removed from the above-mentioned inner needle hub.

As described above, the engaging state of the outer pipe and inner pipe caused by the above-mentioned standing piece is canceled by pulling out the above-mentioned inner needle along the axial direction and in the direction to move the inner needle hub away from the above-mentioned outer needle, so that the arm opening/closing part of the above-mentioned outer pipe can be moved relatively to the inner pipe. Further, the grasp of the plurality of arms on the outer needle hub is released by moving the above-mentioned outer pipe relatively to the inner pipe, and the above-mentioned outer needle hub is removed from the above-mentioned inner needle hub.

That is to say, only by pulling the inner needle from the outer needle, the inner needle can be accommodated inside the inner needle hub, and the outer needle hub can be removed from the inner needle hub.

Further, it is desirable that a groove is formed in the periphery of the above-mentioned outer pipe along the axial direction of the above-mentioned outer pipe, and a projection accommodated in the above-mentioned groove is formed in the outer periphery of the above-mentioned inner pipe, so that the above-mentioned groove and the projection inhibit the outer pipe from moving back and forth relatively to the above-mentioned inner pipe.

In this case, an inner needle hub body can be pulled along the axial direction and in the direction away from the outer needle, since the groove and the projection inhibit the outer pipe from moving back and forth relatively to the inner pipe.

Furthermore, when the locked state of the outer pipe and inner pipe caused by the above-mentioned standing piece is canceled, and the tip of the above-mentioned inner needle passes by the standing piece and is pulled out, it is desirable that the above-mentioned standing piece closes the through hole of the inner needle.

In this case, once the inner needle is accommodated inside the cylinder body, the inner needle does not protrude again out of the cylinder body, since the path (the through hole of the inner needle) of the inner needle towards the outer needle is closed by the standing piece. Therefore, the inner needle can be reliably accommodated inside the inner needle hub.

As described above, according to this preferred embodiment, it is possible to obtain the puncture device in which, only by pulling the inner needle from the outer needle, the inner needle can be accommodated inside the inner needle hub, and the outer needle hub can be removed from the inner needle hub.

Second Preferred Embodiment

Next, a second preferred embodiment will be described with reference to FIGS. 13 to 16. It should be noted that like parts are designated by the same reference signs as in the first preferred embodiment, and will not be described further in detail.

This preferred embodiment improves the above-mentioned first preferred embodiment and prevents the outer needle hub 22 (catheter 2) from moving (rattling) inside the protector 5.

Figure 13:
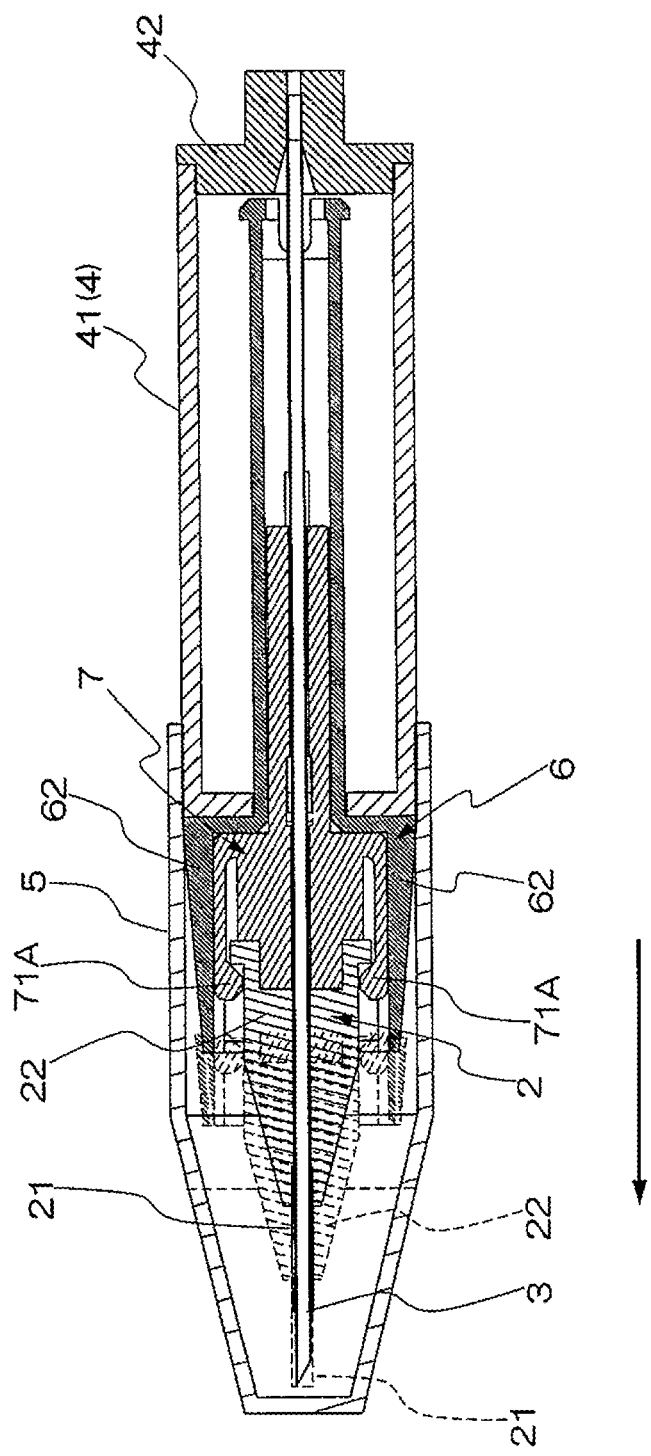
FIG. 13 is a longitudinal sectional view showing the first preferred embodiment, for explaining how the outer needle moves.

Thus, it is possible to solve a problem that, as the outer needle hub 22 moves (rattles) inside the protector 5, the outer needle 21 covers the tip of the inner needle 2 as shown in FIG. 13 by dotted lines so that the puncture cannot be carried out, or the outer needle hub 22 drops out of the inner pipe 7 so that the puncture cannot be carried out.

As shown in FIG. 13, the protector 5 which covers the catheter 2 and the above-mentioned inner needle 3 is fitted and attached to the outer periphery of the inner needle hub 41, while an end of the outer periphery of the arm opening/closing part 62 of the outer pipe 6 is also in pressure contact with the inner periphery of the protector 5. Further, the outer needle hub 22 is retained by the arms 71A of the inner pipe 7, and the arms 71A are in pressure contact with the guide grooves 62A of the arm opening/closing part 62 of the outer pipe 6.

Figure 14:
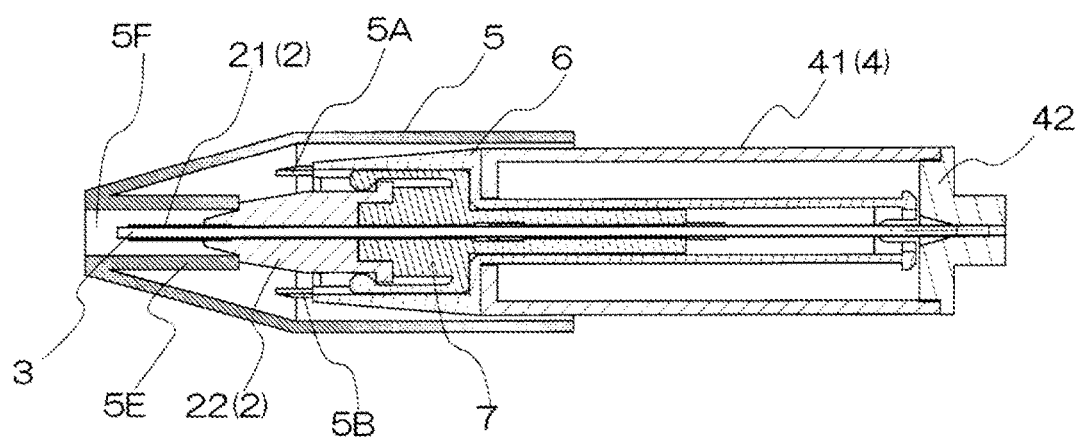
FIG. 14 is a longitudinal sectional view showing a second preferred embodiment.
Figure 15:
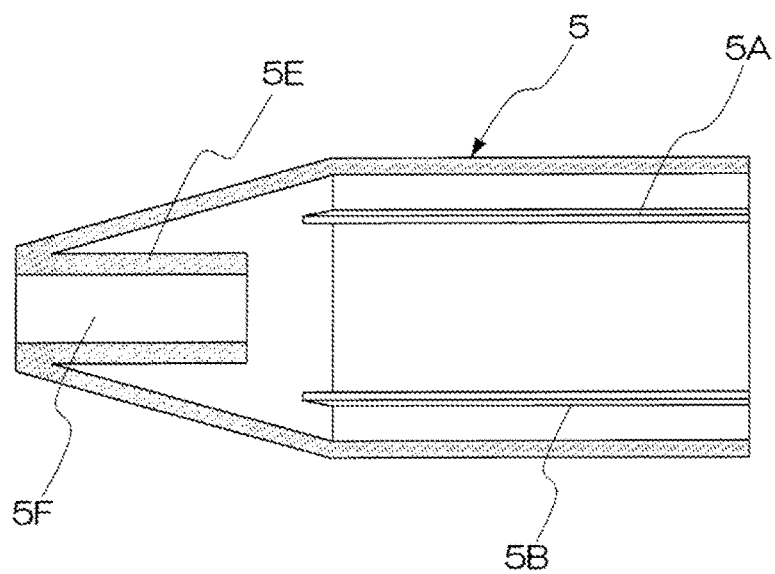
FIG. 15 is a longitudinal sectional view of a protector in accordance with the second preferred embodiment.

As shown in FIGS. 14 to 16, this second preferred embodiment is characterized by providing the inner periphery of the protector 5 with contact portions 5A, 5B, 5C, and 5D which are in pressure contact with the outer periphery of the inner needle hub 41.

These contact portions 5A, 5B, 5C, and 5D project from the inner periphery of the protector 5 and are elongated along the axis of the protector 5 and in parallel with the above-mentioned axis. A plurality of the above-mentioned contact portions 5A, 5B, 5C, and 5D may only be formed. For example, it is preferable that four pieces are provided as illustrated. Further, it is preferable that these contact portions 5A, 5B, 5C, and 5D are not in contact with the outer periphery of the arm opening/closing part 62 of the outer pipe 6. Even if they are in contact, it is preferable that they are not in pressure contact.

It should be noted that, as for the degree of the contact pressure between the outer periphery of the inner needle hub 41 and the contact portions 5A, 5B, 5C, and 5D, a width and a length of a contact portion, the number, etc. are determined in consideration of slide resistance (pulling force) between the outer periphery of the inner needle hub 41 and the contact portions 5A, 5B, 5C, and 5D.

Further, an outer needle hub supporting portion 5E extended in the axial direction is provided in the inner periphery of the tip portion of the protector 5. It is arranged that this outer needle hub supporting portion 5E is formed in the shape of a cylinder, the tip of the above-mentioned inner needle 3 is located in a space 5F provided in the center, and the end portion of the above-mentioned outer needle hub supporting portion 5E is in abutment with the outer needle hub 22.

That is to say, as shown in FIG. 14, in a situation where the protector 5 covers the catheter 2 and the above-mentioned inner needle 3 (in a situation where the protector 5 is mounted), the outer periphery of the inner needle hub 41 is in pressure contact (fitted) with the contact portions 5A, 5B, 5C, and 5D of the protector 5 and the outer needle hub 22 comes into abutment with the outer needle hub supporting portion 5E.

Therefore, in the situation where the protector 5 is mounted, the outer needle hub supporting portion 5E inhibits the outer needle hub 22 (catheter 2) from moving forwards, and the inner needle hub 41 fitted into the protector 5 inhibits the outer needle hub 22 (catheter 2) from moving rearwards.

As a result, the catheter 2 is in a fixed state and the movement of the catheter 2 is inhibited.

Further, in the case where the above-mentioned protector 5 is removed (when it is moved in the direction of the arrow shown in FIG. 13), the above-mentioned contact portions 5A, 5B, 5C, and 5D are not in contact with the arm opening/closing part 62 of the outer pipe 6, or they are not in pressure contact even if they are in contact. Therefore, even if the protector 5 moves, the arm opening/closing part 62 of the outer pipe 6 does not move in the direction of the arrow shown in FIG. 13 and stops in that position.

As a result, when the above-mentioned protector 5 is removed, the outer needle hub 22 (catheter 2) does not move relatively to the inner needle 3. Thus, it is possible to avoid a problem that the outer needle 21 moves beyond the tip of the inner needle 3 to cover the tip of the inner needle 3, for example.

Third Preferred Embodiment

Next, a third preferred embodiment will be described with reference to FIGS. 17, 18, and 19. It should be noted that like parts are designated by the same reference signs as in the first and second preferred embodiments, and will not be described further in detail.

This third preferred embodiment improves the second the above-mentioned preferred embodiment further. It is arranged that the relay pipe which extends the inner pipe is provided between the above-mentioned inner needle hub and the outer pipe, so that the inner needle hub can be further extended from the outer needle.

Figure 17:
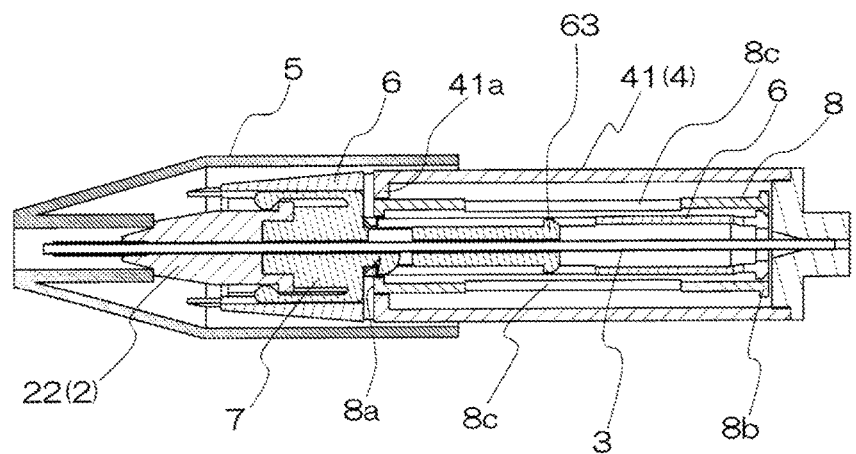
FIG. 17 is a longitudinal sectional view showing a third preferred embodiment.
Figure 18:
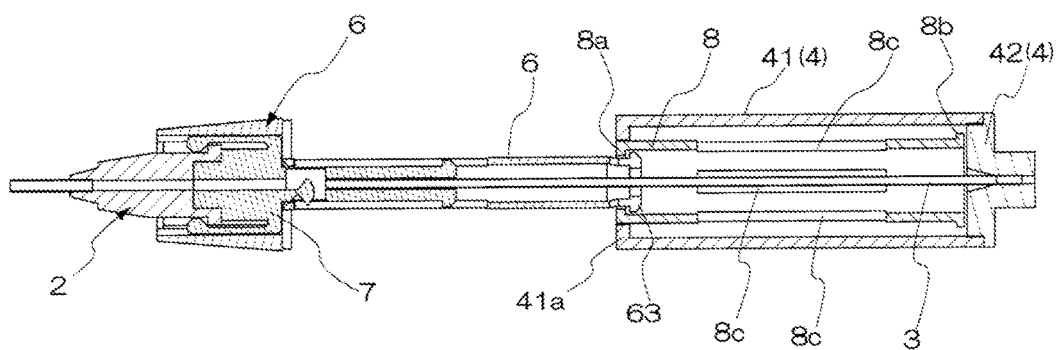
FIG. 18 is a longitudinal sectional view showing a situation where the outer pipe is pulled from the state shown in FIG. 17.

As shown in FIGS. 17 and 18, a relay pipe 8 which extends the outer pipe 6 is provided between the above-mentioned inner needle hub 41 and the outer pipe 6. This relay pipe 8 is formed in the shape of a cylinder, has an outer diameter allowing itself to be accommodated inside the above-mentioned inner needle hub 41, and has an inner diameter allowing the outer pipe 6 to be accommodated in itself. It is arranged that a catch portion 8a is formed at one end of this relay pipe 8 and catches a projection formed at the end portion 63 of the outer pipe 6. Further, it is arranged that a projection 8b is formed at the other end of the relay pipe 8 and caught by a catch portion formed at the end portion 41a of the inner needle hub 41.

Furthermore, an elongate opening 8c is formed in the outer periphery of the above-mentioned relay pipe 8 in parallel with a central axis of the relay pipe 8. Further, the four above-mentioned openings 8c are formed in a circumferential direction of the relay pipe 8.

Thus, flexibility is given to the relay pipe 8 by forming openings 8c in the outer periphery of the above-mentioned relay pipe 8, so that a direction to pull the inner needle hub 41 is an inclined direction (which is not on an extension of the inner needle 3). Even if bending force is applied to the relay pipe 8, it is possible to prevent the relay pipe 8 from being damaged by buckling etc.

Figure 19:
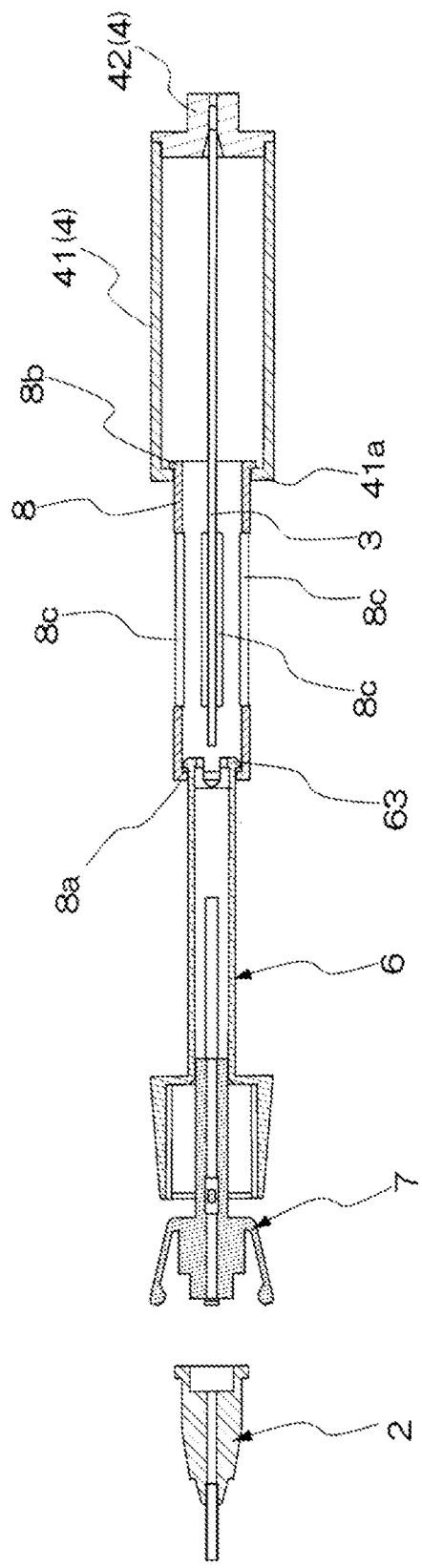
FIG. 19 is a longitudinal sectional view showing a situation where a relay pipe in a state shown in FIG. 18 is pulled out.

As described above, in this third preferred embodiment, as shown in FIG. 19, it is possible to further extend the inner needle hub 4 from the outer needle 21 (catheter 2), and the direction to pull the inner needle hub 41 is not on the extension of the inner needle 3. Therefore, even if the bending force is applied to the relay pipe 8, it is possible to prevent the relay pipe 8 from being damaged by buckling etc.

Fourth Preferred Embodiment

Next, a fourth preferred embodiment will be described with reference to FIGS. 20 and 21. It should be noted that like parts are designated by the same reference signs as in the first preferred embodiment, and will not be described further in detail.

In the above-described first preferred embodiment, in the case where the direction to pull the inner needle hub 41 is the inclined direction (which is not on an extension of the inner needle 3), bending force is applied to the outer pipe 6 (shaft 64 of the outer pipe 6). Therefore, in the case where the outer pipe 6 is formed of a hard synthetic resin material etc., it cannot withstand the bending force, and there is a possibility that the shaft 64 of the outer pipe 6 may be buckled (bent) etc., and damaged Further, in the case where the shaft 64 of the outer pipe 6 is buckled (bent) etc. and damaged etc., there is a possibility that the outer pipe 6 may separate from the inner needle hub 41, and the inner needle 3 may be exposed.

This fourth preferred embodiment improves the above-described first preferred embodiment and is characterized in that at least the outer pipe 6 is formed of a soft synthetic resin material, such as polypropylene.

Figure 20:
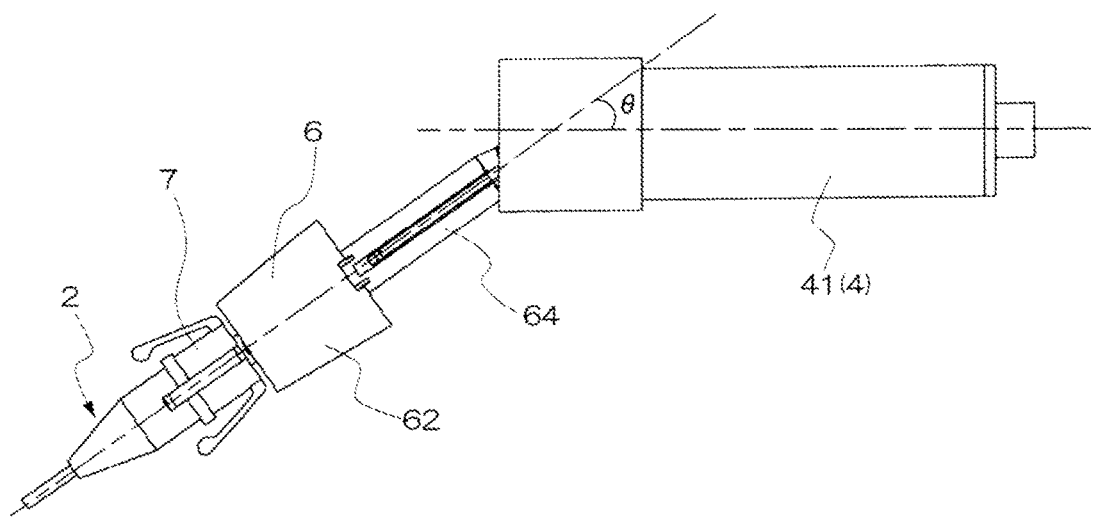
FIG. 20 is a plan view showing a situation where the outer pipe in accordance with a fourth preferred embodiment is pulled out and bent.
Figure 21:
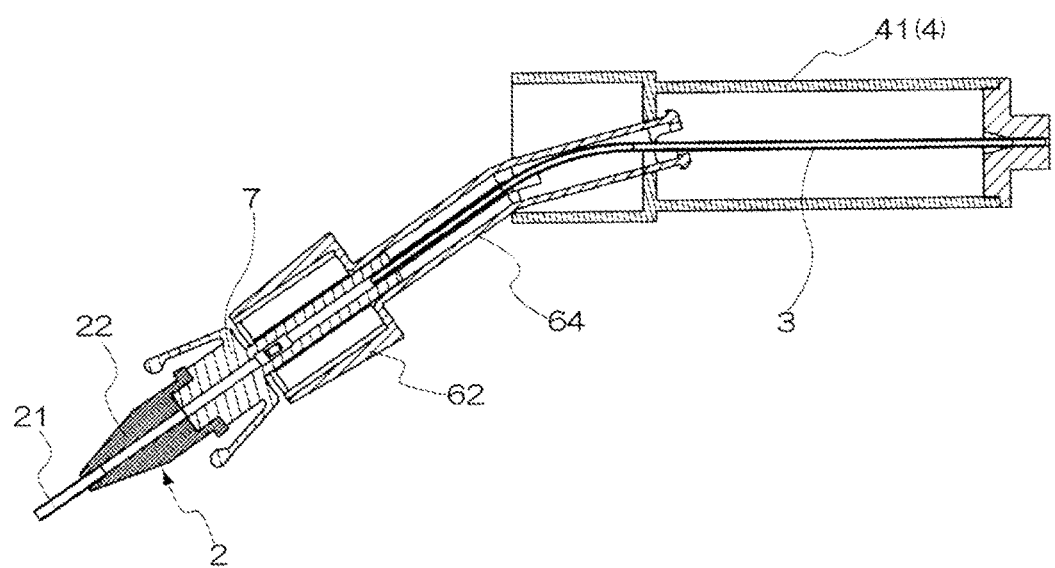
FIG. 21 is a longitudinal sectional view in accordance with the fourth preferred embodiment shown in FIG. 20.

In particular, if the direction to pull the inner needle hub 41 shifts from the extension of the inner needle 3 by an angle θ as shown in FIGS. 20 and 21, the bending force is applied to the shaft 64 of the outer pipe 6.

At this time, since the outer pipe 6 is formed of a soft synthetic resin material, such as the polypropylene, the shaft 64 of the outer pipe 6 is bent by the above-mentioned bending force, but damages, such as a crack etc., can be prevented. Further, as a result of preventing the damage of the shaft 64 of the outer pipe 6 etc., the outer pipe 6 separates from the inner needle hub 41, and the inner needle 3 is unlikely to be exposed.

It should be noted that the soft synthetic resin material for forming the outer pipe 6 preferably has an elongation percentage of 200% or more in compliance with JIS K7113 (Test Method for Tensile Properties of Plastics). In particular, polypropylene is preferred.

Further, in the above-mentioned preferred embodiment, although the case where the outer pipe 6 is formed of a soft synthetic resin material has been described, it is preferable that components other than inner needle 3, in particular the inner needle hub 41, the inner pipe 6, the outer needle hub 22, and the outer needle 21, are also formed of a soft synthetic resin material, such as polypropylene.

As described above, in the case where the inner pipe 6, the outer pipe 7, and the inner needle hub 41 are also formed of a soft synthetic resin material, such as polypropylene, the slide resistance can be reduced and a weak user can also handle it easily. In particular, when polypropylene is used, the pull-out operation of the inner needle hub 41 can be performed with a force of less than 0.8N (Newton).

It should be noted that the relay pipe 8 as described in the third preferred embodiment may be formed of a soft synthetic resin material, such as polypropylene. In this case, the opening 8C as described in the third preferred embodiment need not necessarily be formed.

Fifth Preferred Embodiment

Further, a fifth preferred embodiment will be described with reference to FIGS. 22 and 23. It should be noted that like parts are designated by the same reference signs as in the first and second preferred embodiments, and will not be described further in detail.

This preferred embodiment improves the above-described second preferred embodiment and is characterized in that a gripping part for gripping the device when used by a user is formed at the outer periphery of the inner needle hub to improve the user's convenience.

Figure 22:
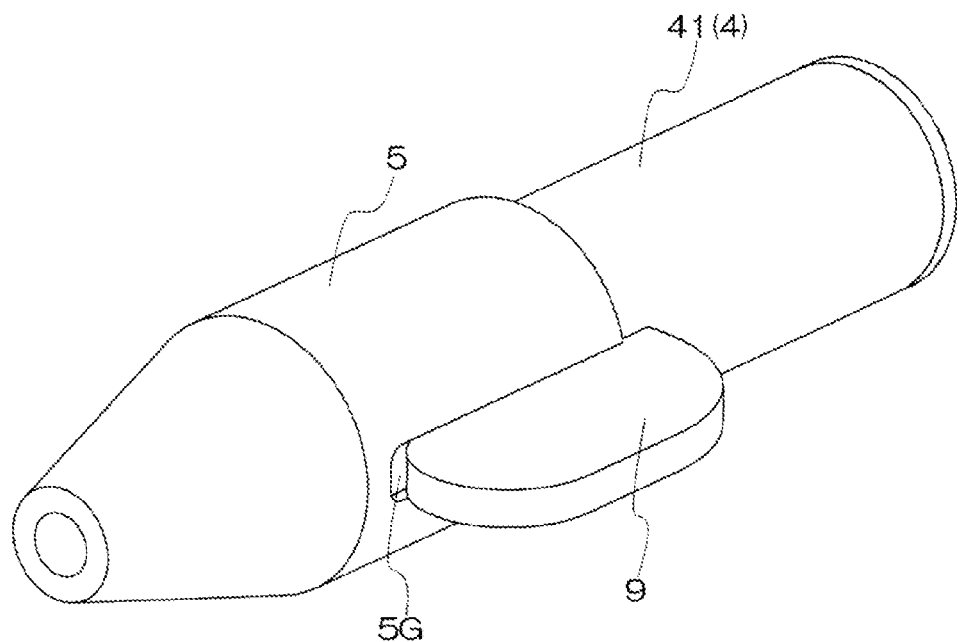
FIG. 22 is a perspective view of a fifth preferred embodiment.

As shown in FIG. 22, the inner needle hub 41 is formed in the shape of a pillar. Therefore, when the protector 5 is removed from the puncture device 1 and a blood vessel (patient's body 110) is punctured with the outer needle 21 and the inner needle 3, it is carried out by holding the main part of the above-mentioned inner needle hub 41 in the shape of a pillar.

However, as is pointed out, it is difficult for some users to perform the puncture operation by holding the outer periphery of the main part of the inner needle hub 41 in the shape of a pillar.

Figure 23:
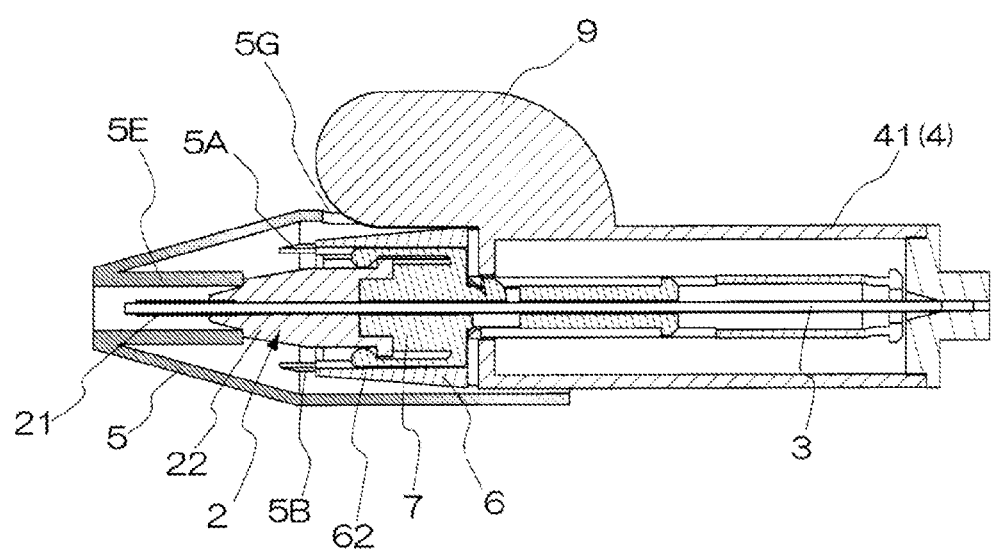
FIG. 23 is a longitudinal sectional view of the fifth preferred embodiment shown in FIG. 20.

As shown in FIGS. 22 and 23, in this fifth preferred embodiment, in parallel with a central axis of the above-mentioned inner needle hub 41, a gripping part 9 for gripping the device is formed in the outer periphery of the tip portion of the inner needle hub 41 in the shape of a pillar. This gripping part 9 is extended from the outer periphery of the tip portion of the inner needle hub 41 towards the catheter 2 (outer needle 21). The tip portion of the above-mentioned gripping part 9 is formed in the position corresponding to the tip portion of the outer pipe 6 (arm opening/closing part 62).

Further, when the protector 5 is mounted on the inner needle hub 41, an opening 5G is provided for the above-mentioned protector 5 in order to avoid collisions between the above-mentioned gripping part 9 and the protector 5. This opening 5G is elongated from an insertion end side (the opposite end side of the outer needle hub supporting portion 5E) of the inner needle hub 41 towards the outer needle hub supporting portion 5E.

Therefore, the inner needle hub 41 can be mounted on the protector 5 without interfering with the gripping part 9, when mounting the protector 5 on the inner needle hub 41.

In the fifth preferred embodiment arranged as above, by gripping the above-mentioned gripping part 9, the user can perform the puncture operation holding a portion closer to the inner needle 3 (outer needle 21) than in the case where the puncture operation is performed holding the inner needle hub 41, whereby a more suitable puncture can be performed.

Sixth Preferred Embodiment

A sixth preferred embodiment will be described with reference to FIGS. 24 to 35. It should be noted that like parts are designated by the same reference signs as in the first to fifth preferred embodiments, and will not be described further in detail.

Incidentally, in the conventional puncture device, when the patient's body 110 is punctured with the outer needle 102*a*, a tip 103*a* of the inner needle 103 needs to project from the tip of outer needle 102*a*. Therefore, there is a demand for putting a cap-like protector on the outer needle 102*a* and the inner needle 103 and for protecting it in terms of safety so that the inner needle 103 and outer needle 102*a* may not shift in the axial direction before using the puncture device.

Figure 24:
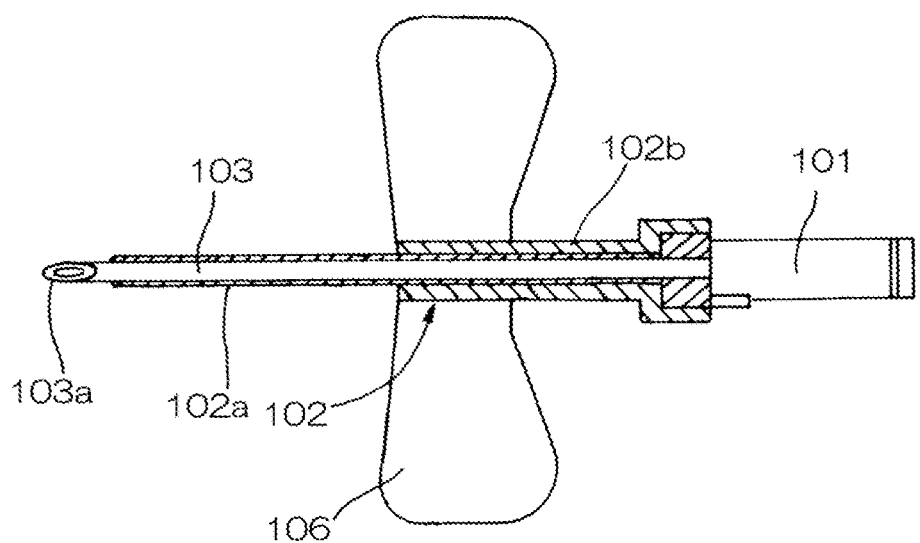
FIG. 24 is a partially sectional view showing a modification of a conventional puncture device.

However, as shown in FIG. 24, in the puncture device where wings 106 are formed at the sides of the outer needle hub 102*b*, the above-mentioned wings 106 serve as an obstacle, when putting the above-mentioned protector. That is to say, there is a problem that the whole outer needle hub 102*b* cannot be covered with the above-mentioned protector. Further, if the protector which can accommodate the wings 106 is formed, there arises a problem that the protector becomes very large in size.

This preferred embodiment has arisen to solve this problem and is characterized in that, even in the case where the wings are provided for the outer needle hub for retaining the outer needle, the protector can reliably be mounted without enlarging the protector for covering the outer needle hub, protect the above-mentioned outer needle and the inner needle projecting from the above-mentioned outer needle, prevent displacements, and secure safety.

Hereinafter, the puncture device in accordance with the sixth preferred embodiment will be described.

Figure 25:
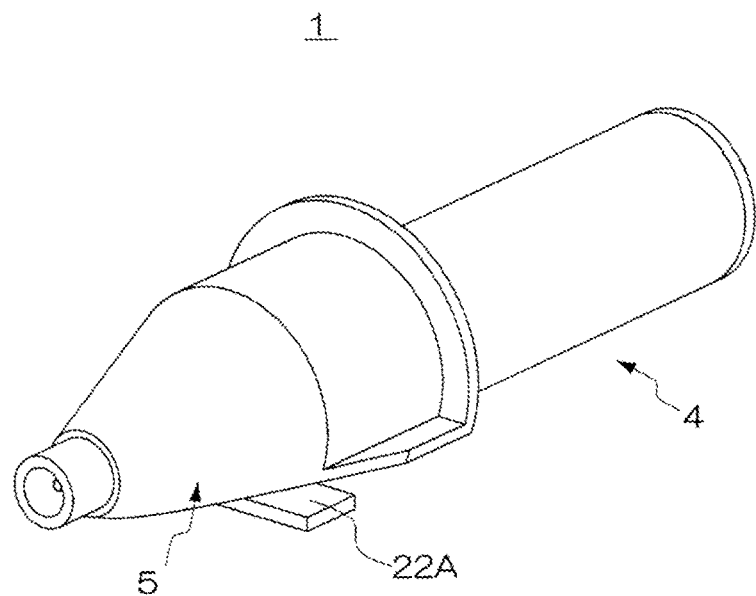
FIG. 25 is a perspective view showing an appearance of the puncture device in accordance with a sixth preferred embodiment of the present invention.
Figure 26:
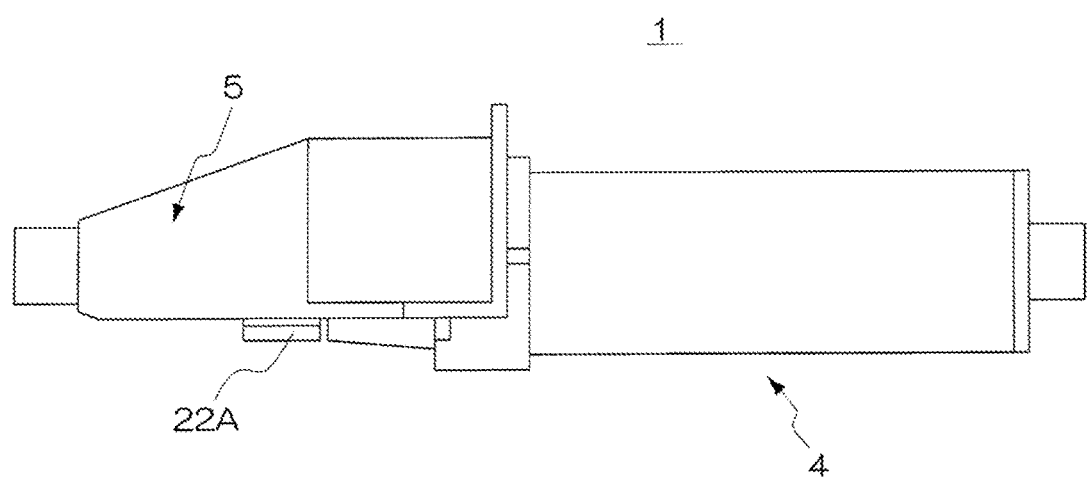
FIG. 26 is a side view of the puncture device of FIG. 25.
Figure 27:
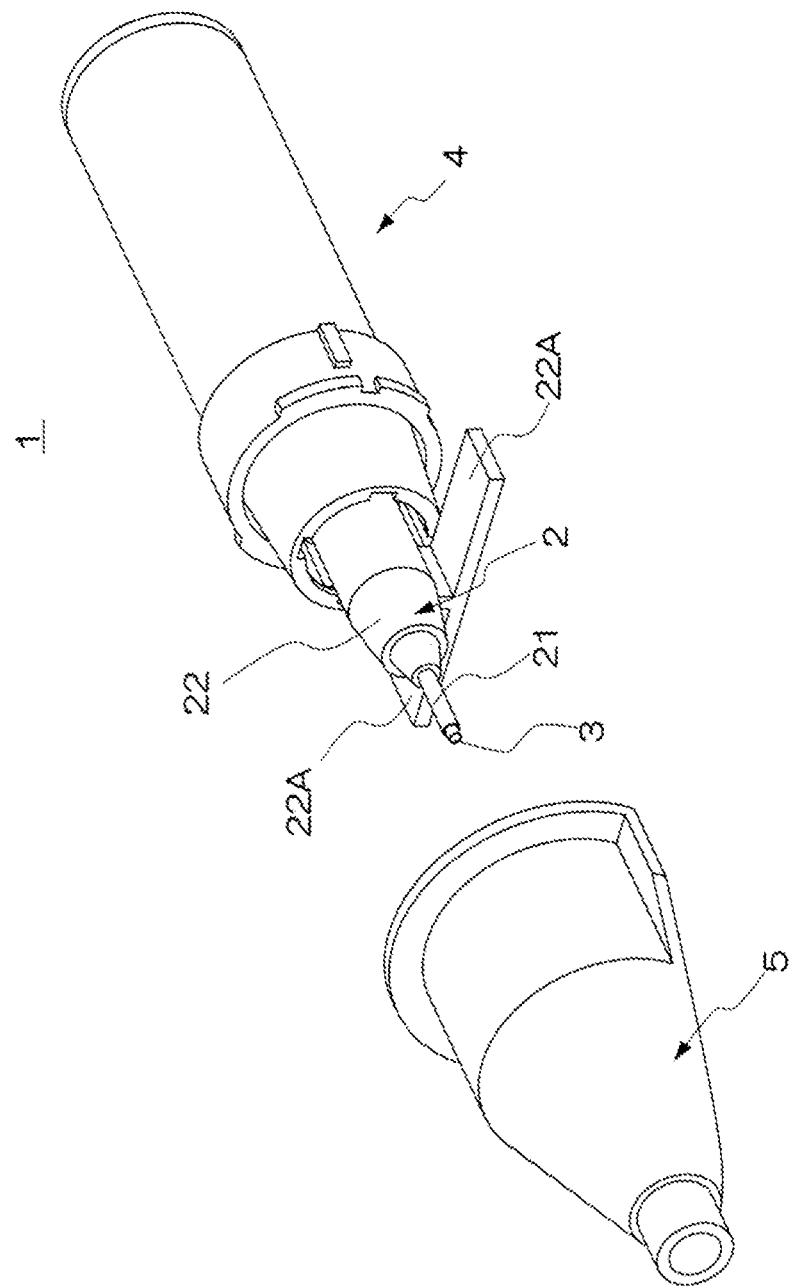
FIG. 27 is a perspective view showing a situation where the protector of the puncture device in FIG. 25 is removed.

As shown in FIGS. 25 to 27, the puncture device 1 is provided with a catheter 2, an inner needle 3 whose tip portion is inserted in the above-mentioned catheter 2, a cylindrical syringe 4 for retaining an end portion (base portion) of the above-mentioned inner needle 3, and a protector 5 for covering the above-mentioned catheter 2 and a tip of the above-mentioned inner needle 3. Further, in the above-mentioned puncture device 1, all the components except the above-mentioned inner needle 3 are made of resin.

Figure 28:
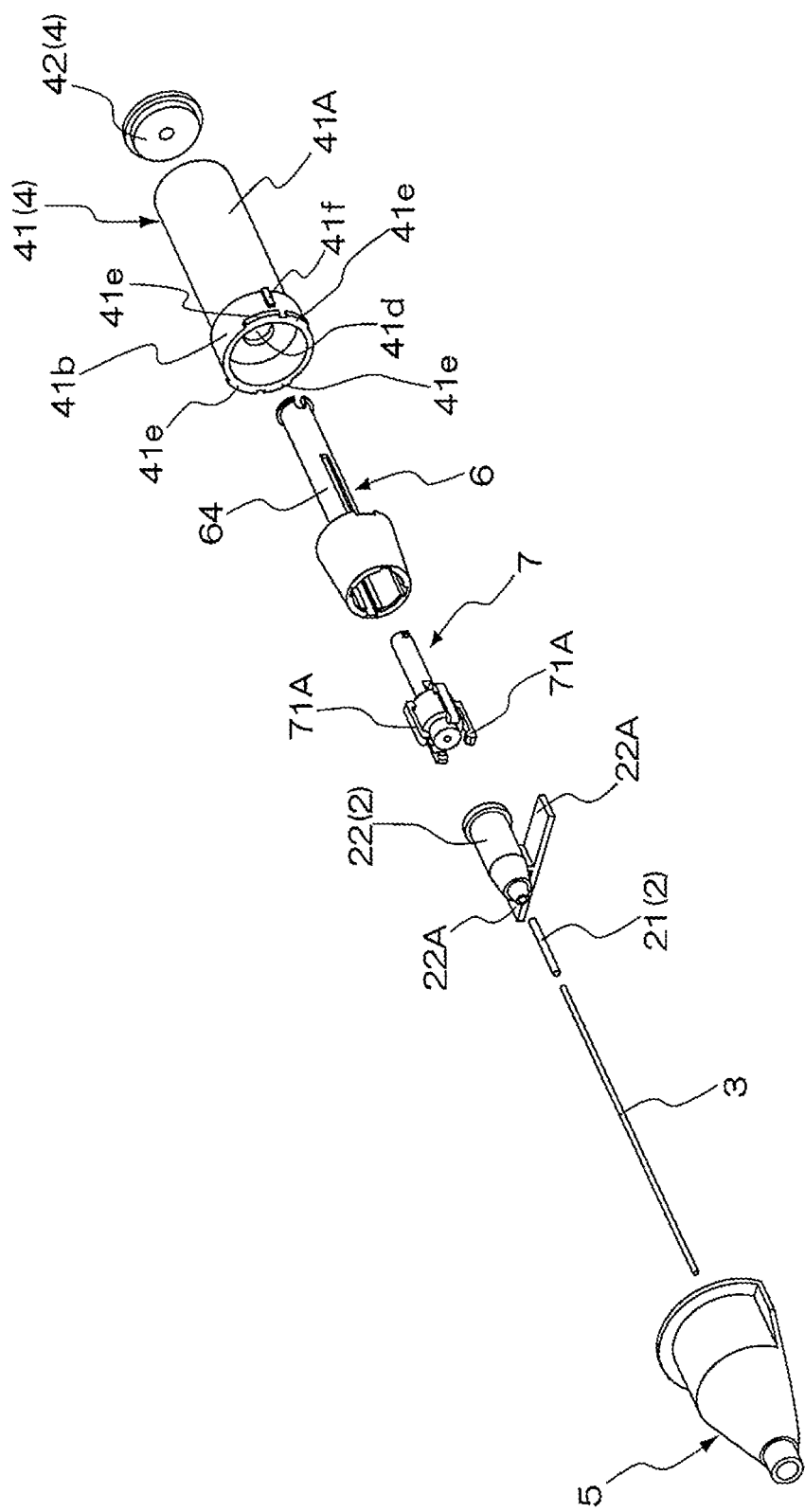
FIG. 28 is a perspective view showing a situation where the puncture device of FIG. 25 is exploded.
Figure 29:
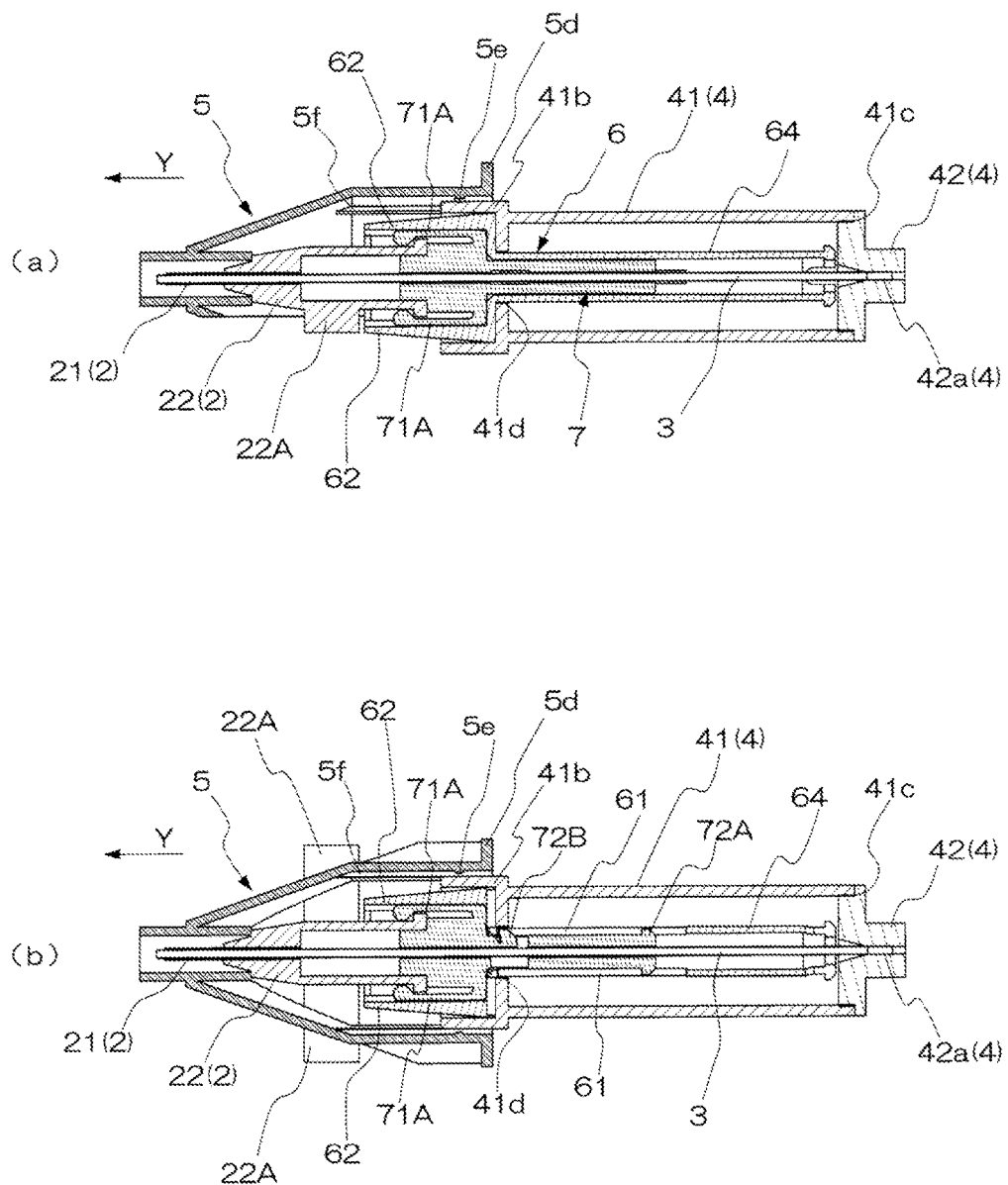

As shown in FIGS. 27 and 28, the above-mentioned catheter 2 has an outer needle 21 formed of a hollow pipe which is flexible and an outer needle hub 22 for retaining a base portion of the outer needle 21. A pair of wings 22A (projecting parts) extending to both the right and left sides are formed integrally with the above-mentioned outer needle hub 22. The above-mentioned pair of wings 22A are attached to a patient's skin with an adhesive tape etc., and are used in order to prevent the displacement of the catheter 2.

The above-mentioned inner needle hub 41 is formed substantially in the shape of a cylinder. As shown in FIGS. 28 to 31, a cylindrical fitting portion 41b whose diameter is larger than that of a main body 41A is formed at the tip side of the above-mentioned inner needle hub 41. This fitting portion 41b is arranged so as to fit the protector 5.

Further, an opening 41c into which a plug 42 is fitted is provided at a rear end portion of the inner needle hub 41. A through hole 41d into which a shaft 64 of the above-mentioned outer pipe 6 is inserted is provided at the main body 41A side of the cylindrical fitting portion 41b. Furthermore, it is arranged that the above-mentioned outer pipe 6 is accommodated in the main body 41A and the fitting portion 41b of the inner needle hub 41.

A plurality of circumferentially arcuate rib-like projections 41e (arcuate, viewed from the tip side) are formed at the tip portion of the outer periphery of the fitting portion 41b (four rib-like projections are illustrated in the figure). The rib-like projections 41e are locked to locked projections 5e (see FIG. 33) formed in the protector 5 so that the protector 5 is mounted (fixed) to the above-mentioned syringe 4.

Figure 30:
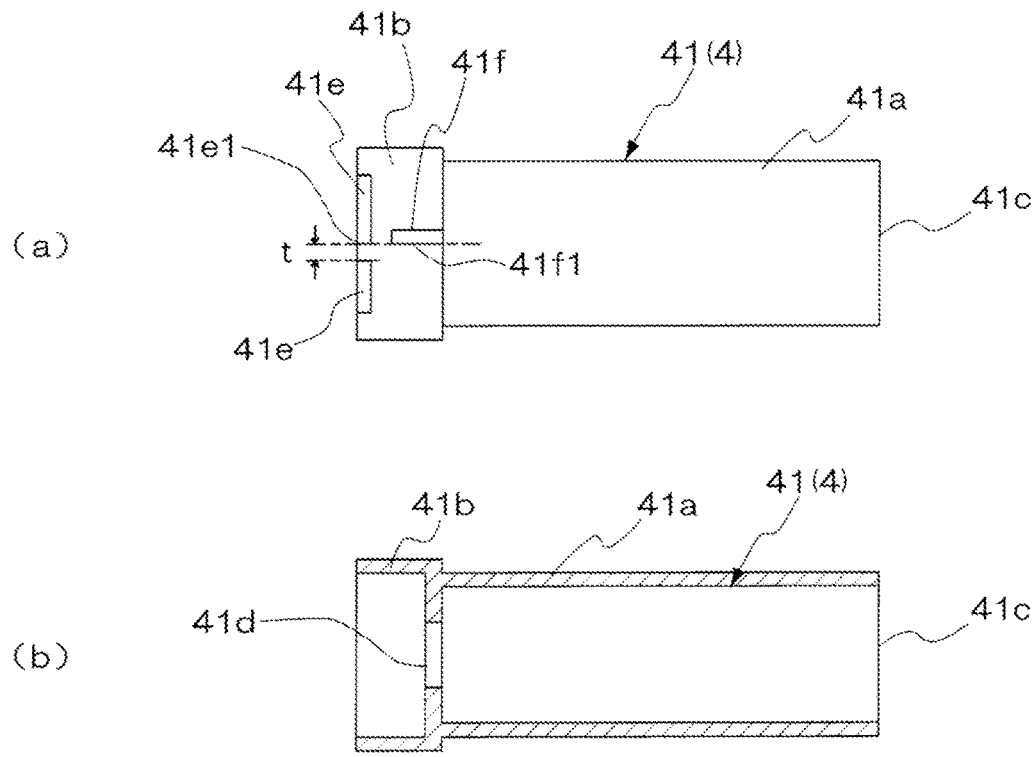

Further, adjoining rib-like projections 41e among the above-mentioned rib-like projections 41e are arranged to have a predetermined gap t as shown in FIG. 30.

That is to say, the four rib-like projection 41e make two pairs of rib-like projections 41e, which are arranged symmetrically from left side to right side, viewed from the tip side of the inner needle hub 41. Further, the gap t between the rib-like projections 41e arranged symmetrically from left side to right side is selected to have a predetermined size so that the guided parts 5h and 5i (see FIG. 33) formed in the protector 5 may pass through the gap.

Furthermore, a bracing projection 41f which is elongated along the axis of the inner needle hub 41 and in parallel with this axis is provided behind the rib-like projections 41e formed in the outer periphery of the above-mentioned fitting portion 41b (closer to the inner needle base end portion than the rib-like projections 41e).

An undersurface 41f1 of the bracing projection 41f is arranged on the extension of an undersurface 41e1 of the upper rib-like projection 41e of a pair of rib-like projections 41e as shown in FIGS. 30.

That is to say, it is arranged that each of the guided projections 5h and 5i formed in the protector 5 may be reliably retained by one of the pairs of the above-mentioned rib-like projections 41e and one of the bracing projections 41f.

Figure 32:
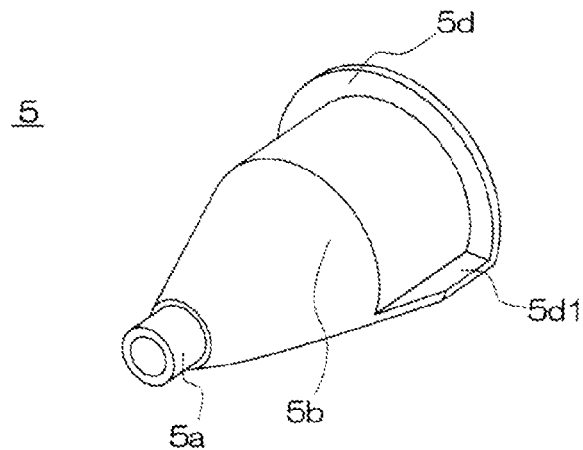
FIG. 32 is a perspective view of the protector.
Figure 33:
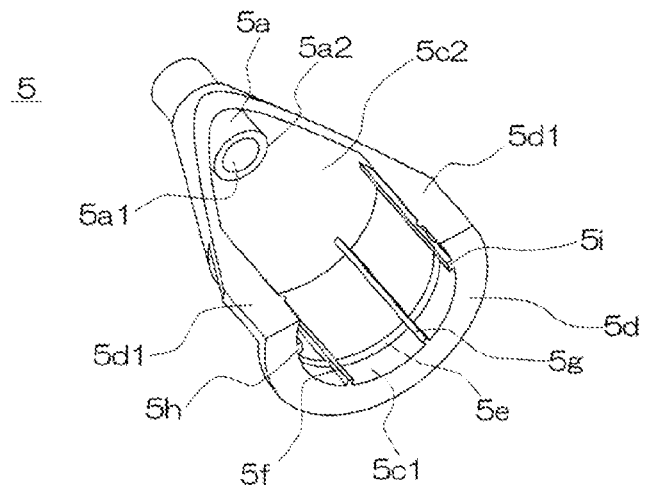
FIG. 33 is a perspective view from a protector bottom (undersurface side).
Figure 34:
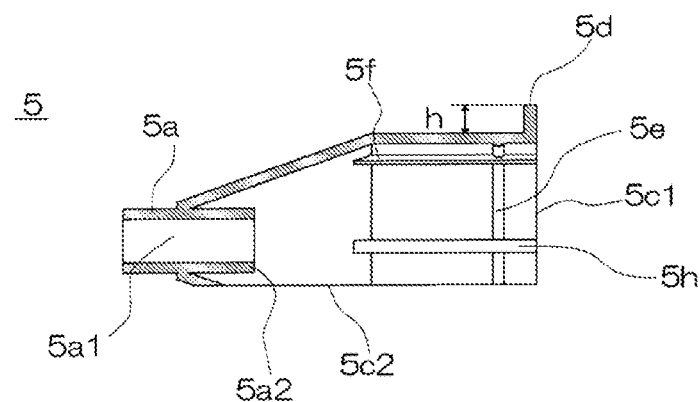
FIG. 34 is a longitudinal sectional view of the protector.

Further, as shown in FIGS. 32 to 34, the above-mentioned protector 5 is provided with a cylindrical outer needle hub supporting portion 5a which accommodates the above-mentioned outer needle 21, and a main body 5b which is extended in the axial direction from the above-mentioned outer needle hub supporting portion 5a to form an upper surface and side faces of the protector and which has openings 5c1 and 5c2 at the opposite end of the above-mentioned outer needle hub supporting portion and in its bottom.

The above-mentioned outer needle hub supporting portion 5a projects and is formed at the inner periphery of the tip portion of the protector 5 in the shape of a cylinder. It is arranged that the tip of the above-mentioned inner needle 3 is located in a space 5a1 of this supporting portion, and an end 5a2 of the above-mentioned outer needle hub supporting portion 5a comes into abutment with the outer needle hub 22.

The above-mentioned opening 5c1 is an opening for inserting the fitting portion 41b of the inner needle hub 41 into the protector 5. The above-mentioned opening 5c2 is formed in order not to interfere with the wings 22A provided for the outer needle hub 22, when the protector 5 is mounted.

Further, an arcuate rib-like frame 5d (arcuate, viewed from cylinder part 5a side) which is extended to both the right and left sides of the above-mentioned main body 5b is formed at the opposite end side of the outer needle hub supporting portion 5a on the above-mentioned main body outer periphery side. Furthermore, for the rib-like frame 5d, extension portions 5d1 are provided extending from both the right and left sides of the above-mentioned main body 5b towards the outer needle hub supporting portion 5a.

Still further, the above-mentioned arcuate rib-like frame 5d has a predetermined height h (size) so that a user may touch and remove the protector 5.

In addition, as the main body 5b is provided with the above-mentioned rib-like frame 5d and the extension portions 5d1 of the rib-like frame 5d, it is possible to increase the mechanical strength of the protector 5 having formed therein the openings 5c1 and 5c2 and prevent the protector 5 from deforming.

Further, the locked projection Se is circumferentially formed on the inner periphery of the protector 5.

When mounting the protector 5 on the above-mentioned inner needle hub 41, as the above-mentioned locked projection Se passes over the rib-like projection 41e formed on the outer periphery of the above-mentioned fitting portion 41b, the locked projection Se of the protector 5 is locked to the rib-like projection 41e, and the protector 5 is fixed to the inner needle hub 41 (fitting portion 41b).

Furthermore, the inner periphery of the protector 5 is provided with contact portions 5f and 5g which come into pressure contact with the outer periphery of the fitting portion 41b of the needle hub 41.

These contact portions 5f and 5g have the structure similar to those of the contact portions 5A to 5D illustrated in the second preferred embodiment. In particular, these contact portions 5f and 5g project from the inner periphery of the protector 5 and are elongated along the axis of the protector 5 in parallel with the above-mentioned axis. A plurality of the above-mentioned contact portions 5f and 5g may only be formed. As for the contact pressure between the outer periphery of the above-mentioned fitting portion 41b and the contact portions 5f and 5g, a width and a length of a contact portion, the number, etc. are determined in consideration of slide resistance (pulling force) between the outer periphery of the above-mentioned fitting portion 41b and the contact portions 5f and 5g.

Incidentally, in the case where the above-mentioned slide resistance (pulling force) is not set up suitably, when the outer periphery of the fitting portion 41b of the inner needle hub 41 is in contact with the whole inner periphery of the main body 5b and when the above-mentioned slide resistance is large, at the moment the user removes the protector with a strong hand, there is a possibility of stabbing the user himself/herself or another person with the inner needle accidentally with too strong a hand. On the other hand, when the above-mentioned slide resistance (pulling force) is small, there is a possibility that the protector 5 may be removed from the fitting portion 41b of the inner needle hub 41.

As described above, by providing the inner periphery of the protector 5 with the contact portions 5f and 5g and suitably setting up the width, the length, the number, etc. of the contact portions, it is possible to suitably obtain the above-mentioned slide resistance (pulling force), and safety can be secured.

Further, the inner periphery of the protector 5 is provided with the guided parts 5h and 5i which are the rib-like projections projecting from the inner periphery of the protector 5 in parallel with the above-mentioned contact portions 5f and 5g (along the axis of the main body 5 in parallel with the above-mentioned axis).

When mounting the protector 5, each of the guided parts 5h and 5i passes between one of the pairs of rib-like projections 41e and is guided by the above-mentioned rib-like projections 41e. Therefore, a thickness of the guided parts 5h and 5i is selected to be smaller than the gap t between the pair of rib-like projections 41e.

Figure 31:
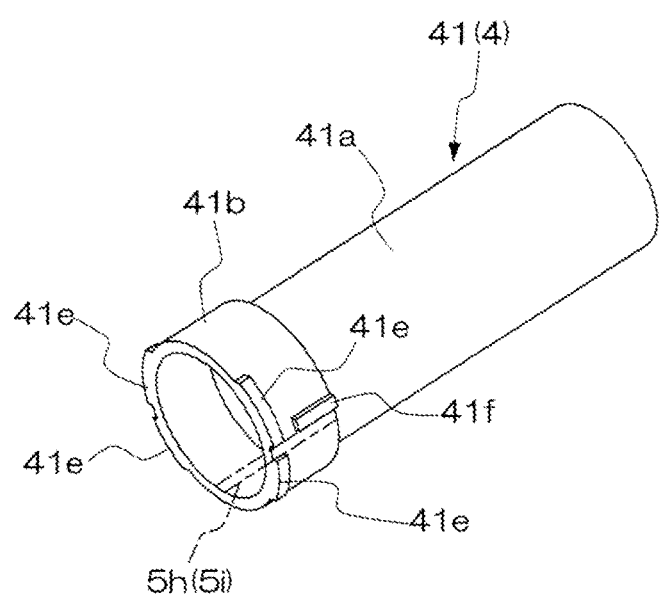
FIG. 31 is a perspective view of the inner needle hub shown in FIG. 26.

Further, an upper surfaces of each of the guided parts 5h and 5i passed between one of the pairs of rib-like projections 41e and guided therewith comes into contact with an undersurfaces of one of the bracing projections 41f formed at the fitting portion 41b of the above-mentioned inner needle hub 41 (see FIG. 31).

Thus, since each of the above-mentioned guided parts 5h and 5i is retained by one of the pairs of the rib-like projections 41e and one of the bracing projections 41f, it is possible to prevent the protector 5 from rattling.

In particular, since the mechanical strength of the opening 5c2 side at the undersurface of the protector 5 is small, there is a possibility that the protector 5 may incline (deform) towards the opening 5c2, when the protector 5 is mounted on the fitting portion 41b of the inner needle hub 41.

As this bracing projections 41f push the above-mentioned guided parts 5h and 5i, it is possible to prevent the inclination (deformation) towards the opening of the protector 5.

Figure 35:
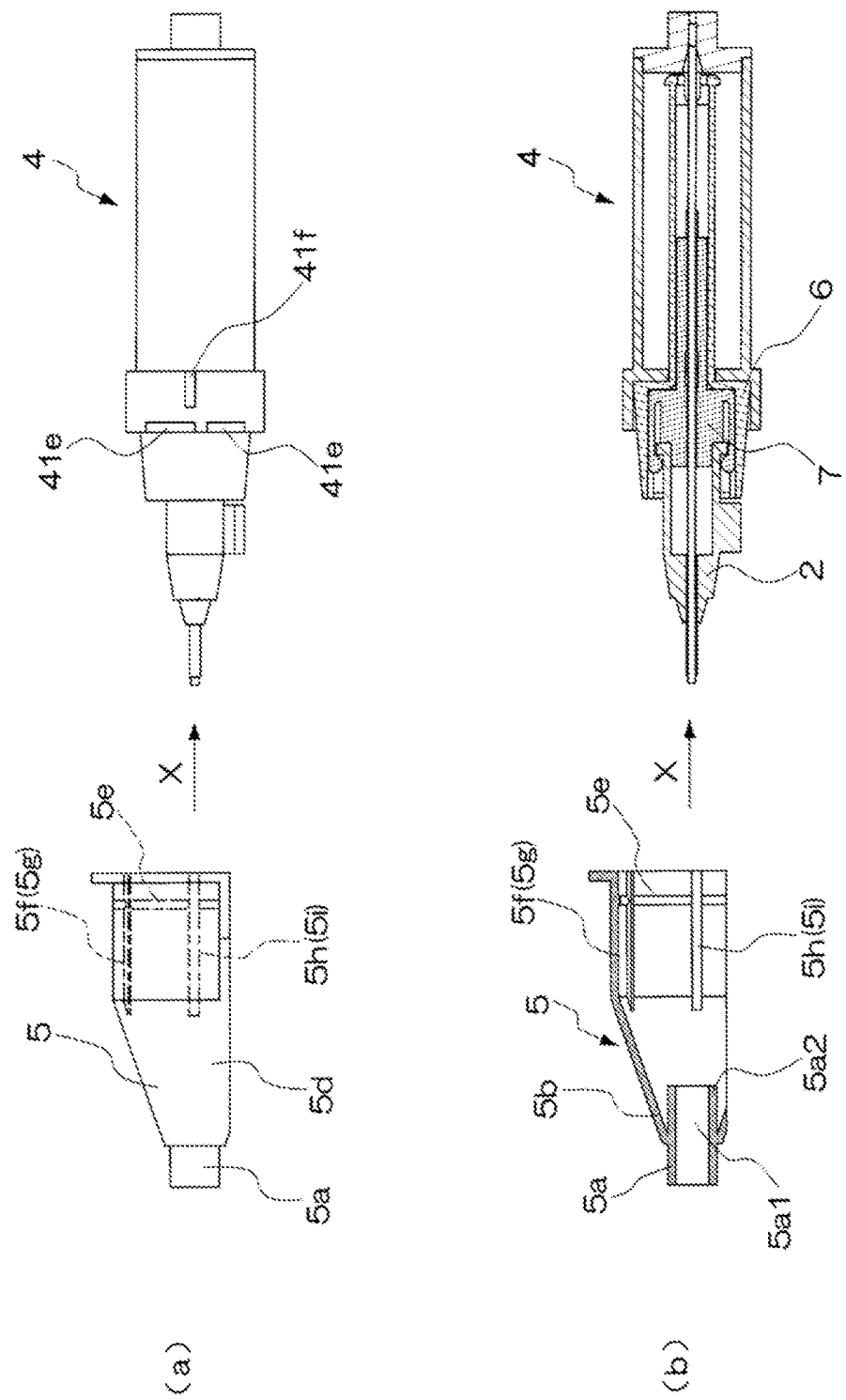

As shown in FIG. 35, when mounting such a protector 5, in a situation where a pair of wings 22A are arranged at the opening 5c2 on the undersurface side of the protector 5, if the protector 5 is moved in the X direction (towards syringe 4) and each of the guided parts 5e and 5h and 5i is passed between one of the pairs of rib-like projections 41e, 41e, then the guided parts 5h and 5i are moved while being guided by the rib-like projections 41e, 41e. Further, the contact portions 5f and 5g move in pressure contact with the outer periphery of the fitting portion 41b of the inner needle hub 41.

Furthermore, as the locked projection 5e of the protector 5 passes over the rib-like projection 41e formed at the outer periphery of the fitting portion 41b of the inner needle hub 41, the locked projection 5e of the protector 5 is locked to rib-like projection 41e, and the protector 5 is fixed to the inner needle hub 41 (fitting portion 41b).

At this time, the upper surface of each of the guided parts 5h and 5i passed between one of the pairs of rib-like projections 41e comes into contact with the undersurface of one of the bracing projections 41f formed at the fitting portion 41b of the above-mentioned inner needle hub 41, and each of the above-mentioned guided parts 5h and 5i is retained by one of the pairs of rib-like projections 41e and one of the bracing projections 41f.

Further, the tip of the above-mentioned inner needle 3 is located in the space 5a1 of the outer needle hub supporting portion 5a formed at the protector 5, and the tip portion 5a2 of the above-mentioned outer needle hub supporting portion 5a comes into abutment with the outer needle hub 22. Thus, the protector 5 is stably mounted (fitted) to the inner needle hub 41.

Furthermore, in a situation where the protector is thus mounted, the forward movement of the outer needle hub 22 (catheter 2) is inhibited by the outer needle hub supporting portion 5a, and the rearward movement of the outer needle hub 22 (catheter 2) is inhibited by the inner needle hub 41 (fitting portion 41b) fixed to the protector 5.

As a result, the catheter 2 is fixed and the movement of the catheter 2 is inhibited. Further, also in the case where the wings 22A are provided for the outer needle hub 22, the protector 5 can reliably be mounted without enlarging. Furthermore, the outer needle 21 and the inner needle 3 projecting from the tip of the outer needle 21 can be accommodated and protected in the space 5a1 of the above-mentioned outer needle hub supporting portion 5a.

Still further, when the above-mentioned protector 5 is removed (when the protector 5 is moved in the Y direction of FIG. 29), the user can touch the rib-like frame 5d and easily remove the protector 5 with one hand. It should be noted that the above-mentioned contact portions 5f and 5g are in contact with the fitting portion 41b but not in contact with the arm opening/closing part 62 of the outer pipe 6, so that the arm opening/closing part 62 of the outer pipe 6 does not move in the Y direction and stops in the position, even if the protector 5 moves.

As a result, even in the case where the above-mentioned protector 5 is removed, the outer needle hub 22 (catheter 2) does not move relatively to the inner needle 3, to thereby avoid a problem that the outer needle 21 moves ahead of the tip of the inner needle 3 and covers the tip of the inner needle 3, for example.

As described above, the puncture device 1 in accordance with this preferred embodiment is a puncture device 1 provided with an outer needle 21, an outer needle hub 22 which retains a base portion of the above-mentioned outer needle and has a projection part on the side, an inner needle 3 whose tip portion is inserted in the above-mentioned outer needle, a cylindrical inner needle hub 41 for retaining the base portion of the above-mentioned inner needle, and a protector 5 for covering the above-mentioned outer needle, wherein the above-mentioned protector 5 has an outer needle hub supporting portion 5a which accommodates the above-mentioned outer needle, a main body 5b which is extended in the axial direction from the above-mentioned outer needle hub supporting portion 5a to form the upper surface and the side faces of the protector and has openings 5c2 and 5c1 respectively at the undersurface and the opposite end of the above-mentioned outer needle hub supporting portion, a rib-like frame 5d formed on the outer periphery at the end opposite the outer needle hub supporting portion of the above-mentioned main body, and a locked projection 5e formed on the inner periphery of the outer needle hub supporting portion at the end opposite the above-mentioned main body, the above-mentioned inner needle hub 41 has a rib-like projection 41e for locking the above-mentioned locked projection 5e formed on the outer periphery at one end, a projection part 22A of the above-mentioned outer needle hub 22 is disposed at the opening of the undersurface of the above-mentioned protector, the locked projection 5e of the above-mentioned main body 5b is locked to the rib-like projection 41e of the above-mentioned inner needle hub 41 by inserting an end of the inner needle hub 41 from the opening 5C1 at an end opposite the outer needle hub supporting portion of the above-mentioned protector 5, and the above-mentioned outer needle 21 is accommodated in the space 5a1 of the above-mentioned outer needle hub supporting portion 5a.

According to such a structure, since the opening 5c2 is formed at the undersurface of the main body 5b of the above-mentioned protector 5, the projection parts (wings 106 etc. shown in FIG. 24) can be provided for the above-mentioned opening 5c2, and the protector 5 can be fitted to the inner needle hub, without interfering with the above-mentioned projection part 22A.

That is to say, even in the case where the projection parts 22A, such as wings, are provided for the outer needle hub 22, the protector 5 can reliably be mounted, without enlarging. The outer needle and the inner needle projecting from the tip of the outer needle can be accommodated and protected in the above-mentioned outer needle hub supporting portion 5a, and it is possible to prevent them from being displaced and secure safety.

It should be noted that since the rib-like frame 5d is formed in the above-mentioned main body 5b, the mechanical strength of the main body 5b can be increased which has the openings 5c2 and 5c1 at the undersurface and the end opposite the above-mentioned outer needle hub supporting portion respectively, and deformation of the protector 5 can be inhibited.

It is desirable that the height from the main body outer periphery of the above-mentioned rib-like frame 5d is set to a size to allow the user to handle it with his/her finger. In the case where the rib-like frame is thus formed, the user can easily remove the protector 5 from the inner needle hub 41 with one hand, touching the rib-like frame 5d.

Further, it is desirable that the above-mentioned protector 5 has the contact portions 5f and 5g which project from the inner periphery of the main body 5b and are extended from the opening at the end opposite the above-mentioned outer needle hub supporting portion 5a along the axis of the main body 5b in parallel with the above-mentioned axis, and that when one end of the inner needle hub 41 (fitting portion 41b) is inserted from the opening 5c1 at the end opposite the outer needle hub supporting portion of the above-mentioned protector 5, the above-mentioned contact portions 5f and 5g come into pressure contact with the outer periphery of the inner needle hub 41 (fitting portion 41b).

As described above, the outer periphery of the inner needle hub 41 (fitting portion 41b) is not in pressure contact with the whole inner periphery of the main body 5b of the protector 5 but in pressure contact with the above-mentioned contact portions 5f and 5g, so that suitable slide resistance can be obtained and it is possible to prevent accidents when mounting and removing the protector 5.

Furthermore, it is desirable that the above-mentioned protector 5 has the guided parts 5h and 5i which project from the inner periphery of the main body 5b and are extended from the opening 5c1 at the end opposite the above-mentioned outer needle hub supporting portion along the axis of the main body 5b in parallel with the above-mentioned axis, and the above-mentioned rib-like projections 41e are formed to have a predetermined gap, and that when one end of the inner needle hub 41 (fitting portion 41b) is inserted from the opening 5c1 at the end opposite the outer needle hub supporting portion of the above-mentioned protector 5, the above-mentioned guided parts 5h and 5i pass between the above-mentioned rib-like projections 41e and are guided by the above-mentioned rib-like projections 41e.

As described above, the protector 5 is guided when mounting the protector 5 on the inner needle hub 41, and reliable fit between the protector 5 and the inner needle hub 41 can be obtained.

It is preferable that the bracing projections 41f with which the above-mentioned guided parts come into contact are formed at the outer periphery of the inner needle hub that is closer to the inner needle base end portion than the above-mentioned rib-like projections 41e.

As described above, as the above-mentioned guided parts 5h and 5i come into pressure contact with the bracing projections 41f, it is possible to prevent the protector 5 from rattling with respect to the inner needle hub 41. In particular, when the protector 5 is mounted on the inner needle hub 41, it is possible to prevent the inclination (deformation) towards the opening of at the under surface of the protector 5.

Seventh Preferred Embodiment

A seventh preferred embodiment will be described with reference to FIGS. 36 to 43. It should be noted that like parts are designated by the same reference signs as in the first to sixth preferred embodiments, and will not be described further in detail. This seventh preferred embodiment improves the protector shown in the sixth preferred embodiment.

Figure 36:
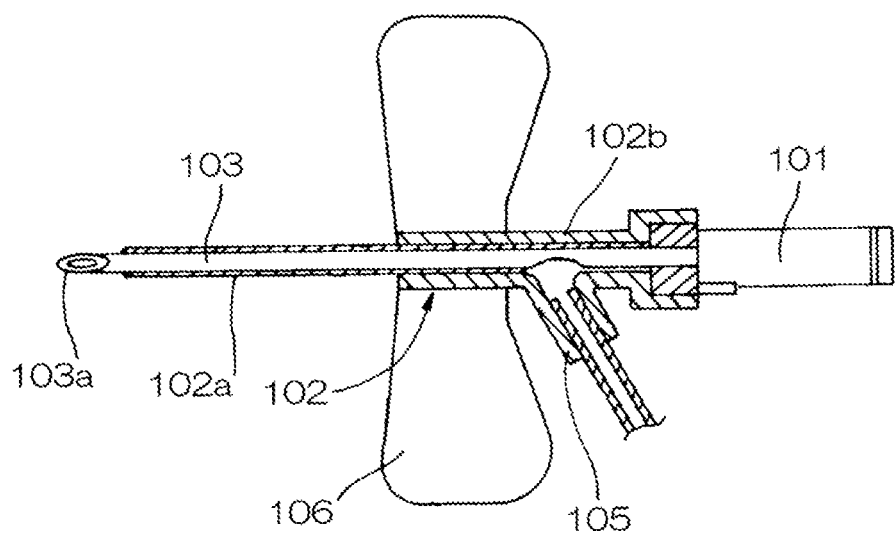
FIG. 36 is a partially sectional view showing a modification of a conventional puncture device.

Incidentally, in addition to the outer needle hub 102b having formed thereon the wings 106 as shown in FIG. 24, there is another outer needle hub 102b having formed thereon a branch pipe 105 at the side face as shown in FIG. 36. When putting such a protector as described above, the above-mentioned projecting branch pipe 105 and wings 106 may serve as an obstacle. That is to say, there is a problem that the whole outer needle hub 102b cannot be covered with the above-mentioned protector. Further, when the protector which can accommodate the branch pipe 105 and wings 106 is formed, there arises a problem that the protector is considerably large in size.

This preferred embodiment arises in order to solve the above-mentioned problems, and the puncture device is characterized in that even in the case where the branch pipe and wings are provided for the outer needle hub for retaining the outer needle, it is possible to reliably mount the protector for covering the outer needle hub without enlarging, protect the above-mentioned outer needle and the inner needle projecting from the above-mentioned outer needle, prevent displacements, and secure safety.

Hereinafter, the puncture device in accordance with a preferred embodiment of the present invention will be described with reference to FIGS. 37 to 43.

Figure 37:
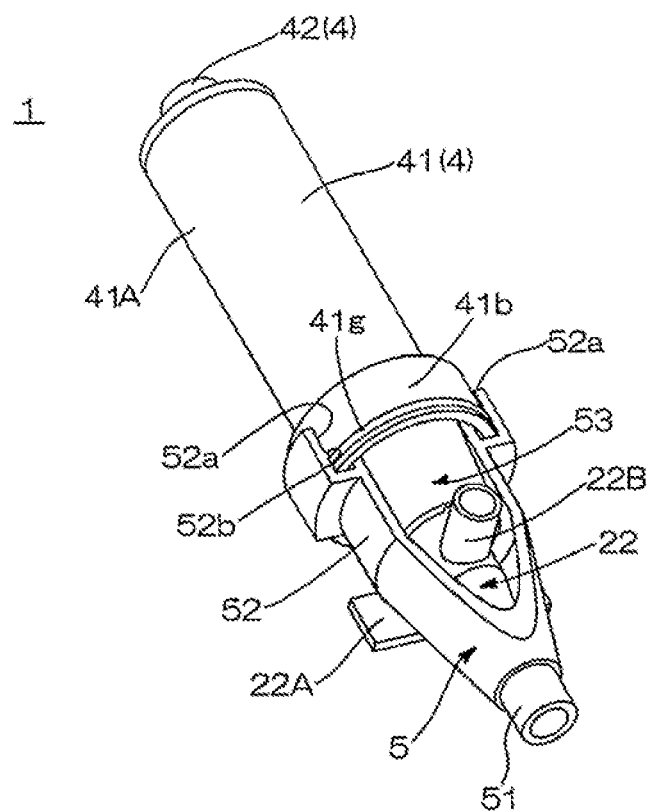
FIG. 37 is a perspective view showing an appearance of the puncture device in accordance with a seventh preferred embodiment of the present invention.
Figure 38:
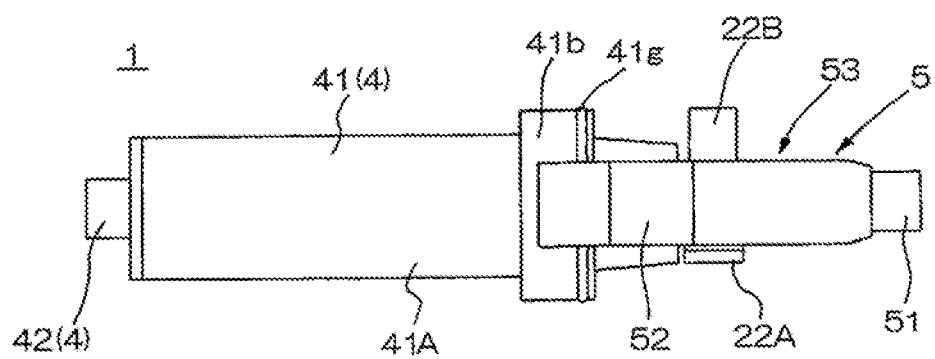
FIG. 38 is a side view of the puncture device of FIG. 37.
Figure 39:
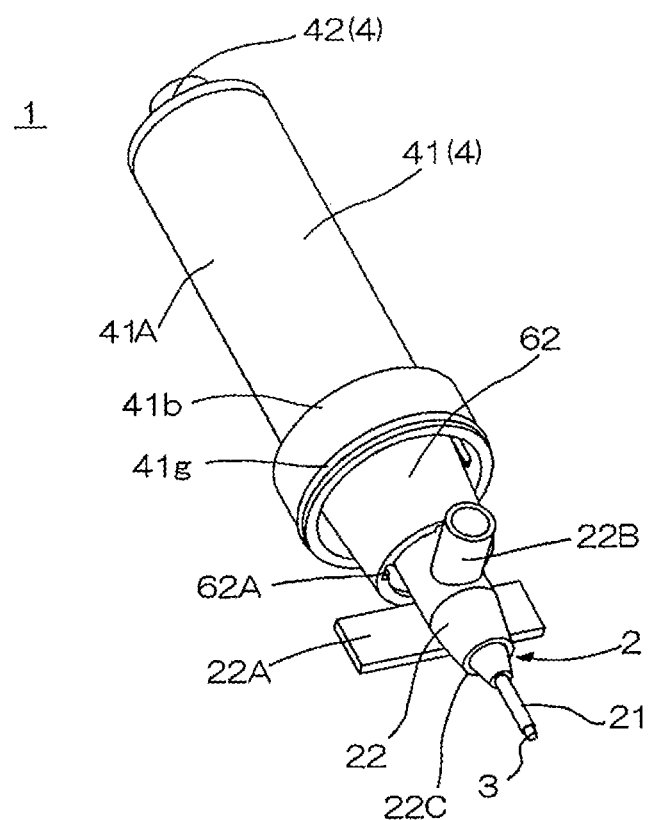
FIG. 39 is a perspective view showing a situation where the protector of the puncture device in FIG. 37 is removed.

As shown in FIGS. 37 to 39, the puncture device 1 is provided with a catheter 2, an inner needle 3 whose tip portion is inserted in the above-mentioned catheter 2, a cylindrical syringe 4 for retaining an end portion (base portion) of the above-mentioned inner needle 3, and a protector 5 for covering the above-mentioned catheter 2 and a tip of the above-mentioned inner needle 3. Further, in the above-mentioned puncture device 1, all the components except the above-mentioned inner needle 3 are made of resin.

As shown in FIG. 39, the above-mentioned catheter 2 has an outer needle 21 formed of a flexible hollow pipe and an outer needle hub 22 for retaining the base portion of the outer needle 21. The above-mentioned outer needle hub 22 has formed thereon a branch pipe 22B (projection part) at the side. Further, a pair of wings 22A (projection parts) are extended from both the right and left sides of the outer needle hub 22, and formed integrally therewith. The above-mentioned branch pipe 22B is for administering a liquid medicine to a patient, and the above-mentioned one pair of wings 22A are fixed to the skin with pressure sensitive adhesive tape etc., and used in order to prevent the displacement of the catheter 2.

Figure 40:
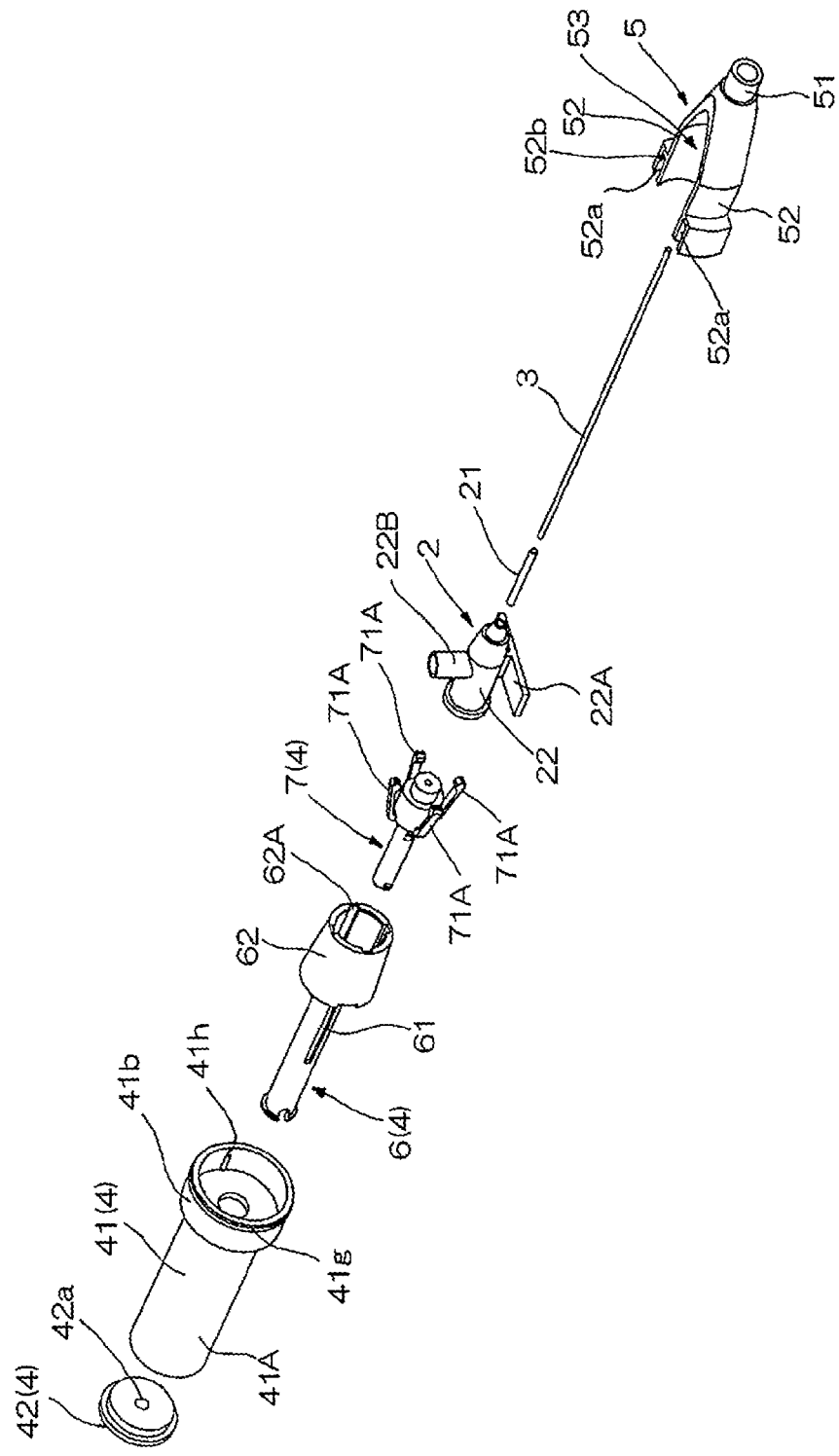
FIG. 40 is a perspective view showing a situation where the puncture device of FIG. 37 is exploded.
Figure 41:
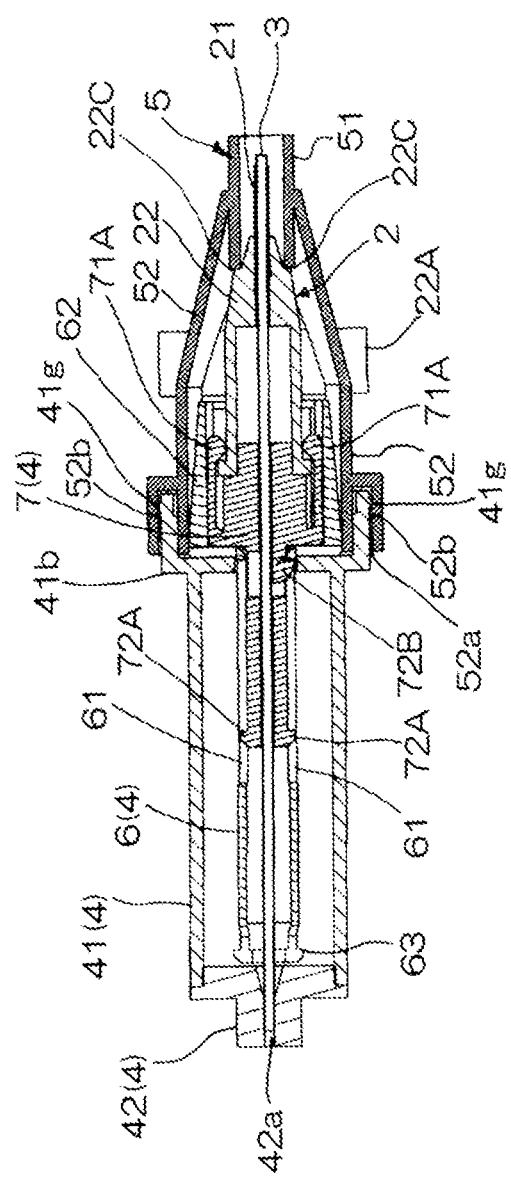
FIG. 41 is a longitudinal sectional view illustrating the puncture device shown in FIG. 37.
Figure 42:
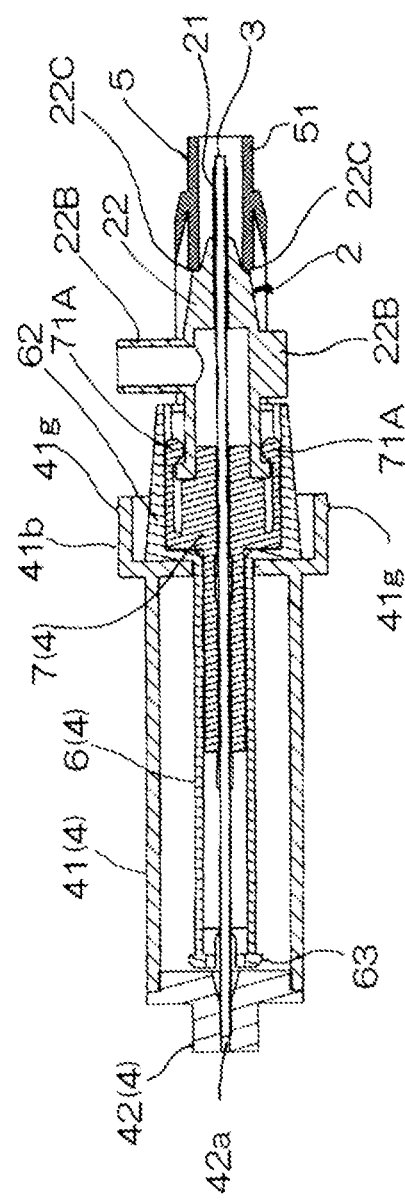
FIG. 42 is a longitudinal sectional view illustrating the puncture device shown in FIG. 37, being different from the longitudinal sectional view of FIG. 41 by 90 degrees in a circumferential direction.

As shown in FIGS. 40 to 42, the above-mentioned syringe 4 is provided with a cylindrical inner needle hub 41, and a plug 42 attached to the base end (left-hand side) of the above-mentioned inner needle hub 41 in a press fit manner and having a substantially cylindrical needle retaining part 42a by which the base portion of the above-mentioned inner needle 3 is retained.

Further, the cylindrical fitting portion 41b whose diameter is larger than that of the main body is formed at the outer periphery of the tip of the above-mentioned inner needle hub 41. A rib-like projection 41g is formed in the shape of a ring along a circumferential direction at the outer periphery of this fitting portion 41b. This rib-like projection 41g is provided in order to fit the inner needle hub 41 to the protector 5 more reliably.

Furthermore, a protrusion 41h that is a rib-like projection extended in the axial direction is formed on the inner periphery of the above-mentioned fitting portion 41b. This protrusion 41h is provided in order to fit the inner needle hub 41 to the protector 5 more reliably and to prevent a circumferential displacement of the protector 5.

Figure 43:
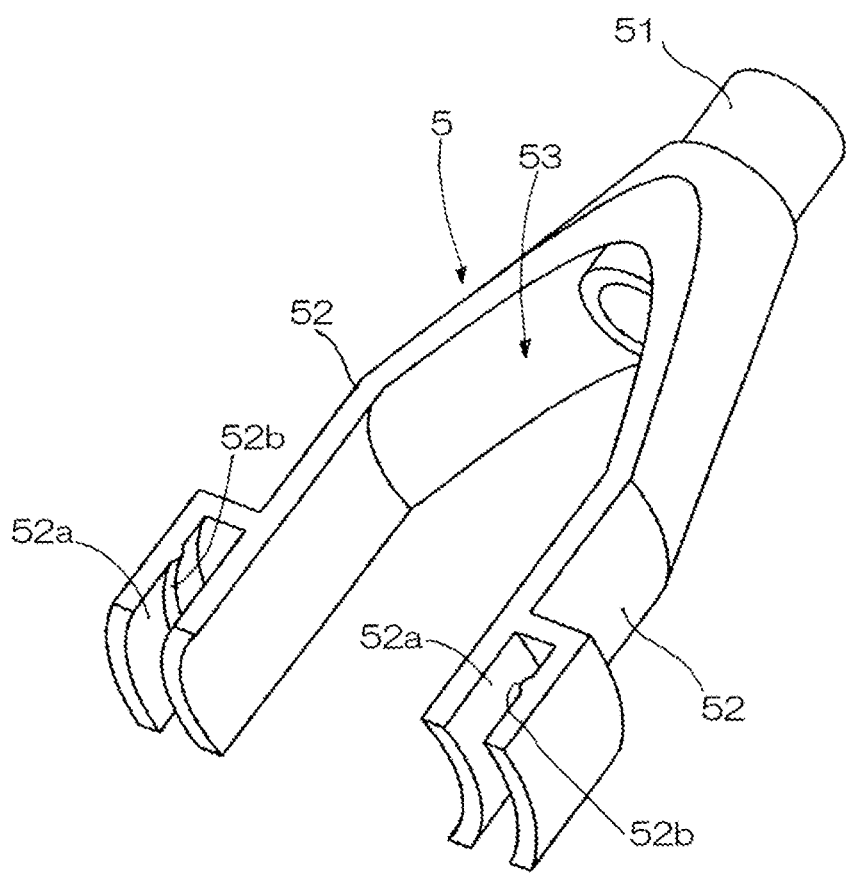
FIG. 43 is a perspective view of a protector.

Still further, as shown in FIG. 43, the protector 5 has a cylindrical outer needle hub supporting portion 51 (see FIGS. 41 and 42) which can accommodate the outer needle 21 and the inner needle 3 projecting from the tip of the outer needle 21, and a pair of supporting legs 52 extended with increasing diameter in the axial direction from the outer periphery of the outer needle hub supporting portion 51. When the protector 5 is mounted to the catheter 2, a rear end of the outer needle hub supporting portion 51 comes into abutment with a step portion 22C formed at the outer needle hub 22, so as to fix the catheter 2.

The above-mentioned one pair of supporting legs 52 are formed by cutting off both the right and left sides of a cap-like hollow cone along the axial direction, for example. Thus, openings 53 are formed between the pair of supporting legs 52 at the side faces of the protector 5.

Further, formed at the tips of the above-mentioned supporting legs 52 are slits 52a curved along a concentric circle of the cylinder part 51 (along the circumferential direction of the fitting portion 41b), and the slits 52a have predetermined length and width. Furthermore, a rib-like projection 52b extended in the circumferential direction is formed on an inner face of the outside wall which forms the slit 52a. This rib-like projection 52b passes over and overlaps (in the axial direction) the rib-like projection 41g of the fitting portion 41b provided for the above-mentioned inner needle hub 41 to carry out the snap-fit. Still further, since the protrusion 41h extended in the axial direction is formed on the inner periphery of the fitting portion 41b as described above, if the above-mentioned fitting portion 41b is fitted into the slit 52a, then the above-mentioned protrusion 41h comes into abutment with the inner face of the slit 52a, so that the displacement in the axial direction of the protector 5 is prevented.

When mounting the protector 5, as shown in FIG. 41, parts of the fitting portion 41b of the inner needle hub 41 are respectively fitted into the slits 52a provided for the ends of the pair of supporting legs 52, and the rib-like projections 52b in the slits 52a are locked to the rib-like projection 41g of the fitting portion 41b, thus leading to a situation where the protector 5 is stably mounted (fitted) to the inner needle hub 41. So, the outer needle 21 and the inner needle 3 projecting from the tip of the outer needle 21 are accommodated in the space of the outer needle hub supporting portion 51 supported by the supporting legs 52 of the protector 5.

Further, as shown in FIGS. 37 and 38, the branch pipe 22B of the outer needle hub 22 is arranged at the upper opening 53 provided on the side of the protector 5, and the pair of wings 22A are arranged at the lower opening 53, so that the supporting legs 52 are fitted to the fitting portion 41b of the inner needle hub 41, without interfering with the above-mentioned branch pipe 22B and the pair of wings 22A.

That is to say, even in the case where the branch pipe 22B or wings 22A are provided for the outer needle hub 22, the protector 5 can reliably be mounted without enlarging, and the outer needle 21 and the inner needle 3 projecting from the tip of the outer needle 21 can be accommodated and protected by the outer needle hub supporting portion 51.

As described above, according to the seventh preferred embodiment in accordance with the present invention, the opening 53 is formed between the supporting legs 52 at the side of the protector 5, so that the branch pipe 22B of the outer needle hub 22 and the pair of wings 22A can be arranged in the above-mentioned opening 53, and the supporting legs 52 can be fitted to the inner needle hub 41, without interfering with the above-mentioned branch pipe 22B and wings 22A.

That is to say, even if the branch pipe 22B or wings 22A are provided for the outer needle hub 22, the protector 5 can reliably be mounted without enlarging, the outer needle 21 and the inner needle 3 projecting from the tip of the outer needle 21 can be accommodated and protected by the outer needle hub supporting portion 51, and it is possible to prevent them from being displaced and secure safety.

Further, in the above-mentioned preferred embodiment, the rib-like projection 52b which projects inwardly is provided on a side face of the slit 52a of the supporting leg 52, the rib-like projection 41g which projects outwardly is provided on an outer face of the fitting portion 41b, these rib-like projections are locked to each other, but the present invention is not limited thereto.

For example, the rib-like projection which projects outwardly along the circumferential direction may be provided on the side face of the slit 52a of the supporting leg 52, and the rib-like projection which projects inwardly along the circumferential direction may be provided on the inner face of the fitting portion 41b, and they may be locked to each other.

In either case, it follows that at least two rib-like projections are interposed between the side face of the slit 52a of the supporting leg 52 and the inner face or the outer face of the fitting portion 41b. Thus, the protector 5 can be firmly fitted to the inner needle hub 41 by locking them mutually.

Alternatively, the rib-like projection which is circumferentially extended can be provided for the slit 52a of the supporting leg 52 or either the inner face or the outer face of the fitting portion 41b.

Even in such an arrangement, it follows that the above-mentioned rib-like projections are interposed between the side face of the slit 52a of the supporting leg 52 and the inner face or the outer face of the fitting portion 41b. Thus, the above-mentioned fitting portion 41b can be fitted into the above-mentioned slit 52a.

Further, the preferred embodiments above are such that the protrusion 41h (rib-like projection) extended in the axial direction is provided on the inner face of the fitting portion 41*b*, and this protrusion 41*h* is interposed between the inner face of the slit 52*a* and the inner face of the fitting portion 41*b*.

However, the present invention is not limited to the above structure, but the protrusion extending in the axial direction may be provided on the inner face of the slit 52*a* of the supporting leg 52, for example, and it may be interposed between the inner face of the slit 52*a* and the inner face or the outer face of the fitting portion 41*b*.

Alternatively, the protrusion extending in the axial direction may be provided on the outer face of the fitting portion 41*b*, and it may be interposed between the inner face of the slit 52*a* and the outer face of the fitting portion 41*b*.

In any structure, the protrusion 41*h* can be interposed between the side face of the slit 52*a* of the supporting leg 52 and the inner face or the outer face of the fitting portion 41*b*, and the above-mentioned fitting portion 41*b* can be fitted into the above-mentioned slit 52*a*.

As described above, the puncture device 1 in accordance with the seventh preferred embodiment is a puncture device provided with an outer needle 21, an outer needle hub 22 which retains the base portion of the above-mentioned outer needle 21 and has a projection part on the side face, an inner needle 3 whose tip portion is inserted in the above-mentioned outer needle 21, a cylindrical inner needle hub 41 for retaining the base portion of the above-mentioned inner needle, a protector 5 for covering the above-mentioned outer needle, wherein the above-mentioned protector 5 has an outer needle hub supporting portion 51 which accommodates the above-mentioned outer needle 21, and a supporting leg 52 which is extended in the axial direction from the above-mentioned outer needle hub supporting portion 51 to form the side face of the protector and has an opening 53 at the side face, a fitting portion 41*b* formed along a circumferential direction of the inner needle hub is provided on one end side of the above-mentioned inner needle hub 41, a slit 52*a* which is formed along a circumferential direction of the above-mentioned fitting portion 41*b* and has predetermined length and width is provided on one end side of the above-mentioned supporting leg 52, projection parts 22A and 22B of the above-mentioned outer needle hub 22 are arranged at an opening at a side face of the above-mentioned protector 5, part of the above-mentioned fitting portion 41*b* is fitted into the slit 52*a* of the above-mentioned supporting leg 52, and the above-mentioned outer needle 21 is accommodated in a space of the above-mentioned outer needle hub supporting portion 51.

According to such a structure, since the opening 53 is formed at the side face of the above-mentioned protector 5, the projection parts 22A and 22B (branch pipe, wings, etc.) can be provided for the above-mentioned opening 53, and the supporting legs 52 can be fitted to the inner needle hub 41, without interfering with the above-mentioned projection parts 22A and 22B.

That is to say, even in the case where the projection parts 22A and 22B, such as the branch pipe and wings, are formed at the outer needle hub 22, the protector 5 can reliably mounted without enlarging, the outer needle 21 and the inner needle 3 projecting from the tip of the outer needle can be accommodated and protected by the above-mentioned outer needle hub supporting portion 51, and it is possible to prevent them from being displaced and secure safety.

In addition, it is desirable that a plurality of the above-mentioned supporting legs 52 are extended from the above-mentioned portion outer needle hub supporting portion 51 along the axial direction, and the above-mentioned opening 53 is formed between a plurality of the above-mentioned supporting legs 52.

Thus, by forming a plurality of supporting legs 52, a plurality of openings 53 can be formed at the side faces of the protector 5 in the circumferential direction, and a plurality of projection parts can be provided for these openings 53.

Further, it is desirable that the rib-like projections 52*b* and 41*g* extending along a circumferential direction are respectively formed on the side face of the slit 52*a* of the above-mentioned supporting leg 52 and the inner face or the outer face of the above-mentioned fitting portion 41*b*, and the above-mentioned rib-like projections 52*b* and 41*g* are interposed between the side face of the slit 52*a* of the above-mentioned supporting leg 52 and the inner face or the outer face of the above-mentioned fitting portion 41*b*, and they are engaged mutually.

As the thus engaged rib-like projections 52*b* and 41*g* are provided, it is possible to more reliably prevent the protector 5 from falling off the inner needle hub 41.

Alternatively, the rib-like projection extending along a circumferential direction may be provided at the side face of the slit 52*a* of the above-mentioned supporting leg 52 or at either the inner face or the outer face of the above-mentioned fitting portion 41*b*, and the above-mentioned rib-like projection may be disposed between the side face of the slit 52*a* of the above-mentioned supporting leg 52 and the inner face or the outer face of the above-mentioned fitting portion 41*b*, and the above-mentioned fitting portion 41*b* may be fitted into the slit 52*a* of the above-mentioned supporting leg 52.

As described above, by providing the rib-like projection extending in the circumferential direction at the side face of the slit 52*a* of the above-mentioned supporting leg 52 or at either the inner face or the outer face of the above-mentioned fitting portion 41*b*, it is possible to obtain the effect of preventing the protector 5 from falling off the inner needle hub 41.

Further, it is desirable that the rib-like projection 41*h* extending in the axial direction is provided at the side face of the slits 52*a* of the above-mentioned supporting leg 52, or at either the inner face or the outer face of the above-mentioned fitting portion 41*b*, the above-mentioned rib-like projection 41*h* is interposed between the side face of the slit 52*a* of the above-mentioned supporting leg 52 and the inner face or the outer face of the above-mentioned fitting portion 41*b*, and the above-mentioned fitting portion 41*b* is fitted into the slit 52*a* of the above-mentioned supporting leg 52.

As describe above, by providing the rib-like projection 41*h* extending in the axial direction, it is possible to prevent the protector 5 from being displaced in the axial direction.

Eighth Preferred Embodiment

An eighth preferred embodiment will be described with reference to FIGS. 44 to 50. It should be noted that like parts are designated by the same reference signs as in the first to seventh preferred embodiments, and will not be described further in detail. This eighth preferred embodiment improves the protector illustrated in the seventh preferred embodiment.

Hereinafter, the puncture device in accordance with the eighth preferred embodiment of the present invention will be described with reference to FIGS. 44 to 50.

As for this puncture device 1, a cylindrical fitting portion 41*b* whose diameter is larger than that of the main body 41A is formed at the tip side of the inner needle hub 41 integrally therewith (or the portion is firmly fitted to the main body 41A, if it is not integral with the inner needle hub 41). A pair of opposed locking hole portions 41b1 which are penetrated in the axial direction are formed on the outer periphery of this fitting portion 41b. The above-mentioned pair of locking hole portions 41b1 protrude radially outwardly from the outer periphery of the fitting portion 41b respectively, and have a predetermined length along a circumferential direction of the fitting portion 41b. It should be noted that the above-mentioned pair of locking hole portions 41b1 are formed in order to fit the inner needle hub 41 to the protector 5.

Figure 49:
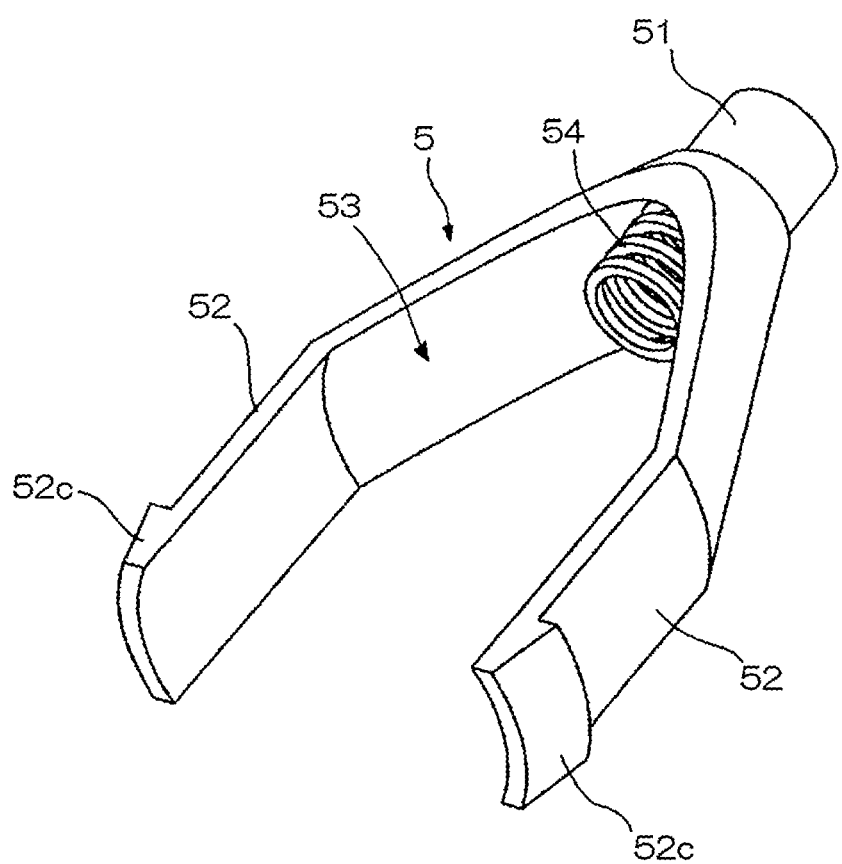
FIG. 49 is a perspective view of a protector.
Figure 50:
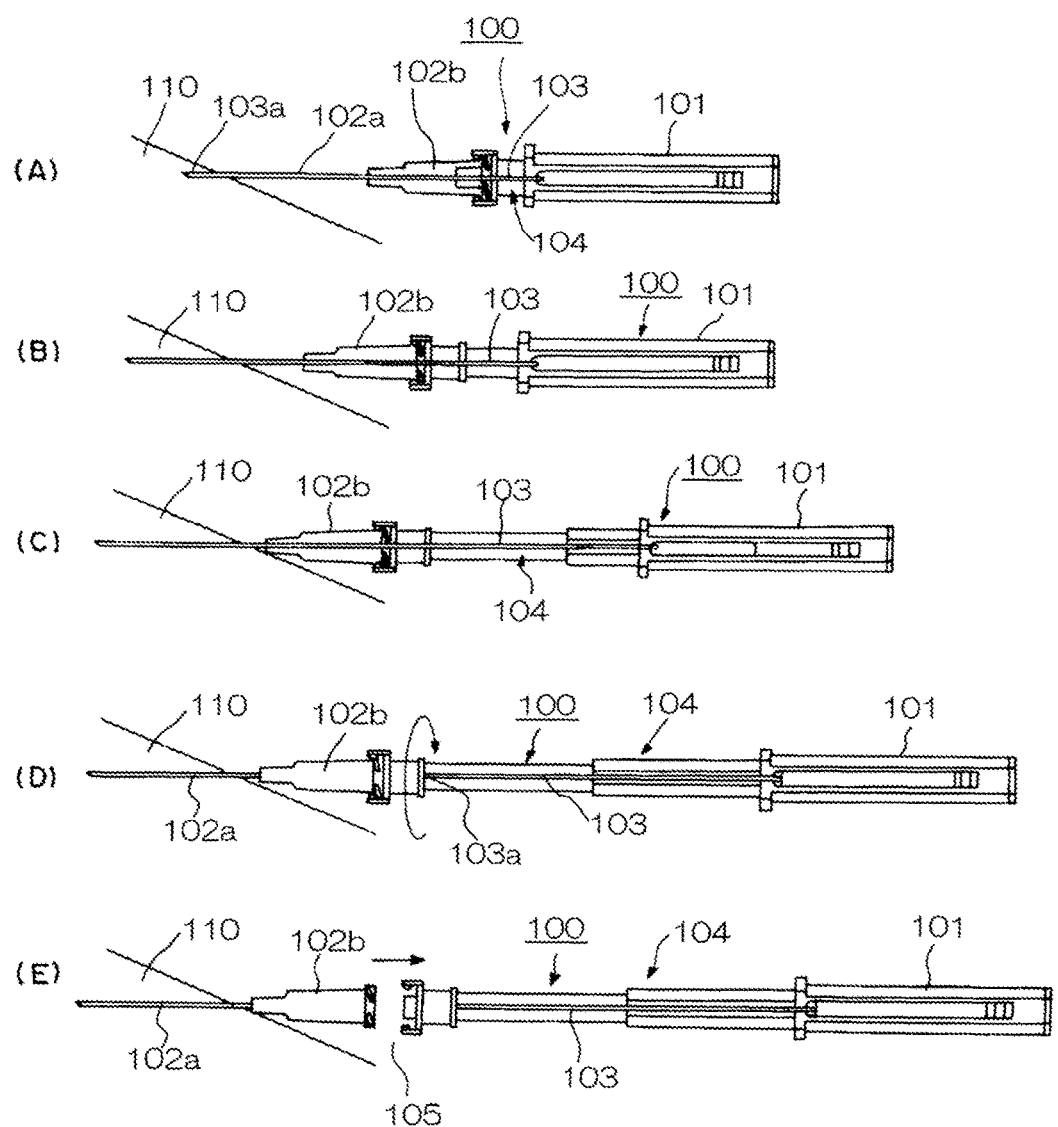
FIG. 50 are side views for explaining how the conventional puncture device works.

Further, as shown in FIG. 49, the protector 5 has a cylindrical outer needle hub supporting portion 51 (see FIGS. 47 and 48) which can accommodate the inner needle 3 projecting from the outer needle 21 and the tip of the outer needle 21, and a pair of supporting legs 52 extended with increasing diameter in the axial direction from the outer periphery of the outer needle hub supporting portion 51. The above-mentioned pair of supporting legs 52 are formed by cutting off both the right and left sides of a cap-like hollow cone along the axial direction, for example. Thus, openings 53 are formed between the pair of supporting legs 52 at the sides of the protector 5.

Furthermore, the above-mentioned supporting leg 52 is provided, at its tip, with a locking member 52c which is formed and curved concentrically about the outer needle hub supporting portion 51 (along the circumferential direction of fitting portion 41b), and the locking member 52c has a predetermined length in the circumferential direction.

In particular, the locking member 52c is sized such that it can be inserted into the locking hole portion 41b1 provided for the inner needle hub 41, and is fitted into the locking hole portion 41b1 as it is completely inserted into locking hole portion 41b1. Further, widths in the radial direction of the above-mentioned locking member 52c and the above-mentioned locking hole portion 41b1 are arranged such that, after the above-mentioned locking member 52c is fitted into the locking hole portion 41b1, the locking member 52c can forcibly be depressed radially inwardly so as to be disengaged from the locking hole portion 41b1.

Furthermore, one end of a spring 54 (elastic component) which is compressible in the axial direction is provided at the rear end of the outer needle hub supporting portion 51. When the protector 5 is mounted, the other end of this spring 54 comes into abutment with a step portion 22C formed in the outer needle hub 22 and the spring is compressed (see FIGS. 47 and 48).

Figure 47:
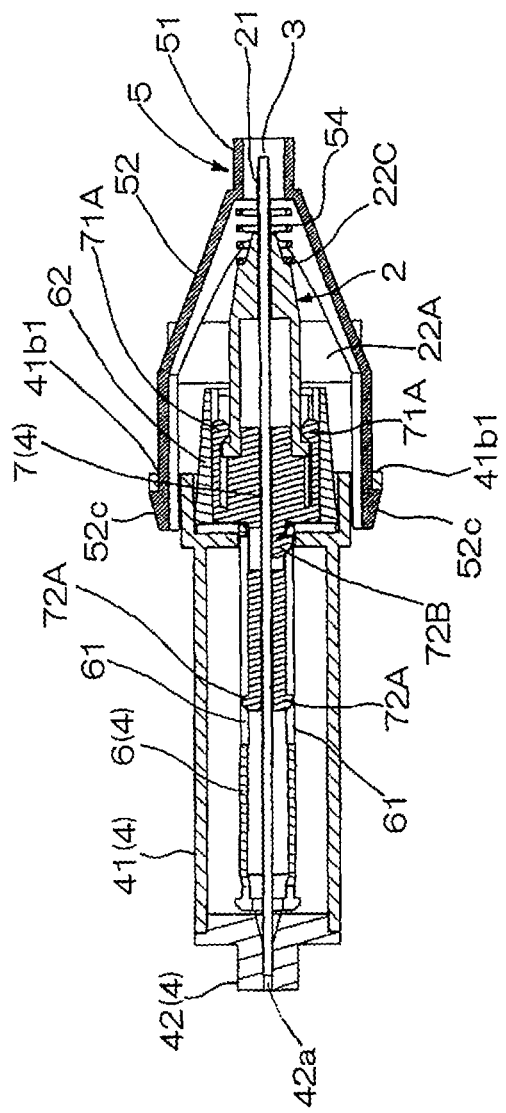
FIG. 47 is a longitudinal sectional view showing the puncture device shown in FIG. 44.
Figure 48:
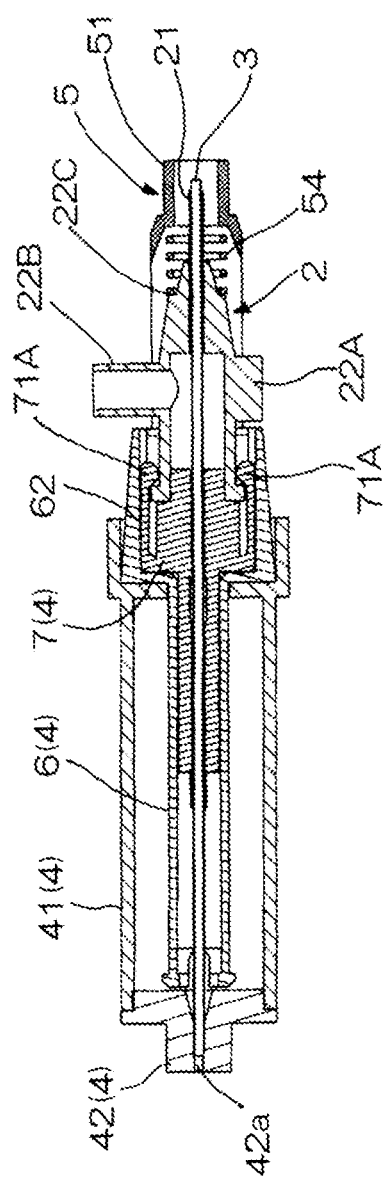
FIG. 48 is a longitudinal sectional view illustrating the puncture device shown in FIG. 44, being different from the longitudinal sectional view of FIG. 47 by 90 degrees in a circumferential direction.

As shown in FIG. 47, when mounting the protector 5, the locking members 52c formed in the pair of supporting legs 52 provided for the protector 5 are inserted and fitted into the locking hole portions 41b1 respectively provided for the fitting portions 41b of the inner needle hub 41. At this time, the spring 54 is compressed between the outer needle hub supporting portion 51 and the outer needle hub 22, to produce biasing force in the direction to separate the protector 5 from the inner needle hub 41, leading to a situation where the protector 5 is firmly and stably mounted (fitted) to the inner needle hub 41. So, the outer needle 21 and the inner needle 3 projecting from the tip of the outer needle 21 are accommodated by the outer needle hub supporting portion 51 supported by the supporting legs 52 of the protector 5.

Figure 44:
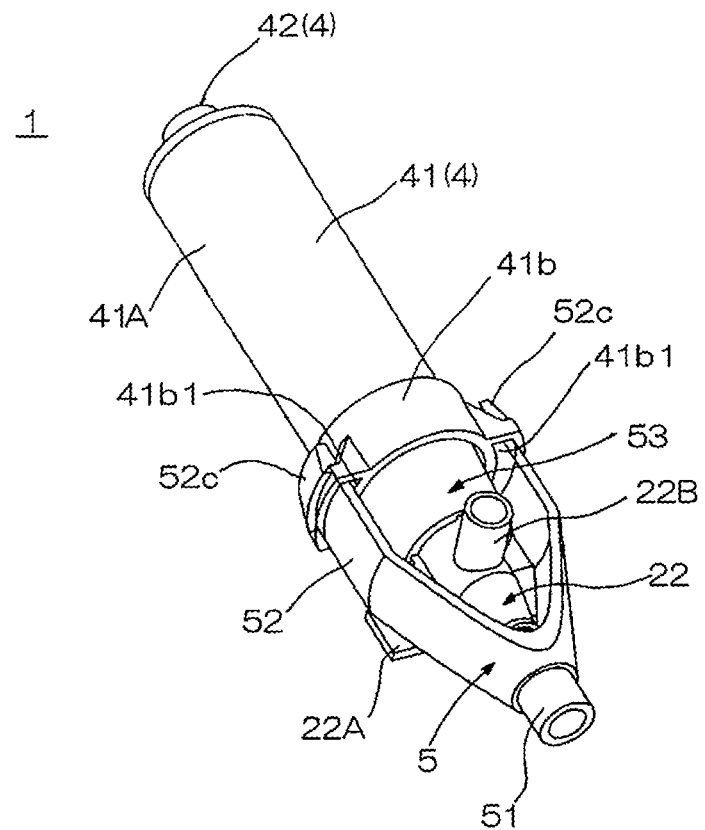
FIG. 44 is a perspective view showing an appearance of the puncture device in accordance with an eighth preferred embodiment of the present invention.
Figure 45:
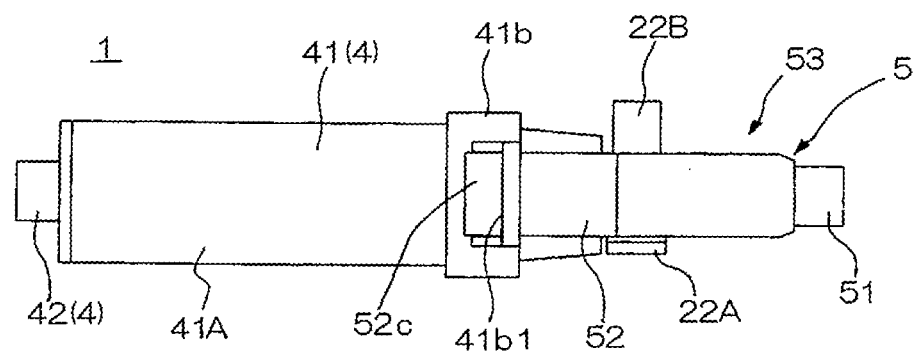
FIG. 45 is a side view of the puncture device of FIG. 1.
Figure 46:
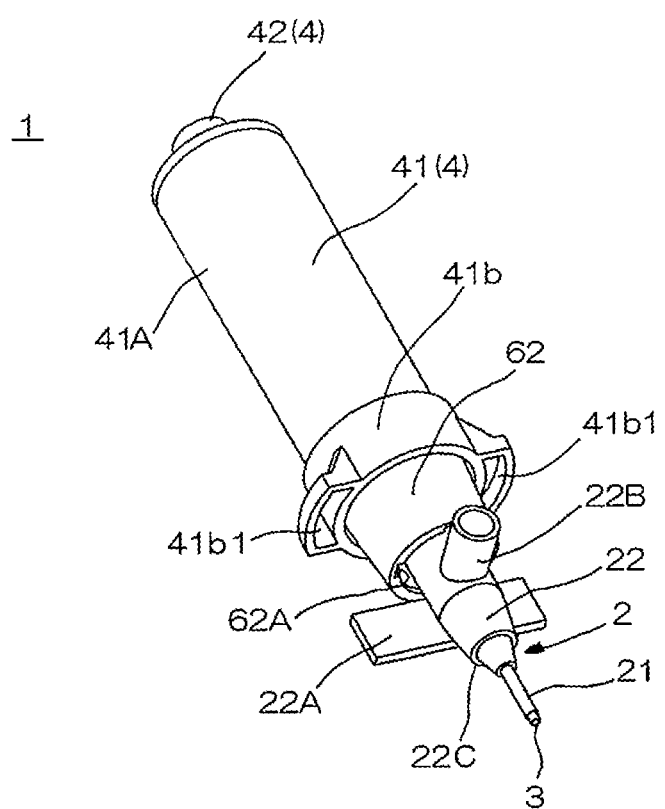
FIG. 46 is a perspective view showing a situation where the protector of the puncture device in FIG. 1 is removed.

Further, as shown in FIGS. 44 and 45, since the branch pipe 22B of the outer needle hub 22 and the pair of wings 22A are arranged at the opening 53 provided at the side of the protector 5, the supporting leg 52 is fitted to the fitting portion 41b of the inner needle hub 41, without interfering with the above-mentioned branch pipe 22B and the pair of wings 22A.

That is to say, even if the branch pipe 22B or wings 22A are provided for the outer needle hub 22, the protector 5 can reliably be mounted, and the outer needle 21 and the inner needle 3 projecting from the tip of the outer needle 21 can be accommodated and protected by the outer needle hub supporting portion 51.

Furthermore, when the above-mentioned protector 5 is removed, the locking member 52c at the tip of the supporting leg 52 is depressed radially inwardly to become disengaged from the locking hole portion 41b1 of the inner needle hub 41. When the above-mentioned locking member 52c is disengaged from the above-mentioned locking hole portion 41b1, the above-mentioned locking member 52c easily falls out of the above-mentioned locking hole portion 41b1 because of the biasing force of the spring 54. Further, the protector 5 is separated from the inner needle hub 41 by pulling out the protector 5 relatively to the inner needle hub 41 in the axial direction (direction to separate).

As described above, according to one preferred embodiment in accordance with the present invention, since the opening 53 is formed between the supporting legs 52 at the side of the protector 5, the branch pipe 22B of the outer needle hub 22 and the pair of wings 22A can be disposed at the above-mentioned opening 53, and the supporting legs 52 can be fitted to the inner needle hub 41, without interfering with the above-mentioned branch pipe 22B and wings 22A.

That is to say, even if the branch pipe 22B or wings 22A are provided for the outer needle hub 22, the protector 5 can reliably be mounted without enlarging, the outer needle 21 and the inner needle 3 projecting from the tip of the outer needle 21 can be accommodated and protected by the outer needle hub supporting portion 51, and it is possible to prevent them from being displaced and secure safety.

As described above, the puncture device 1 in accordance with the eighth preferred embodiment is a puncture device provided with an outer needle 21, an outer needle hub 22 which retains the base portion of the above-mentioned outer needle and has a projection part on the side face, an inner needle 3 whose tip portion is inserted in the above-mentioned outer needle 21, a cylindrical inner needle hub 41 for retaining the base portion of the above-mentioned inner needle, a protector 5 for covering the above-mentioned outer needle, wherein the above-mentioned protector 5 has an outer needle hub supporting portion 51 which accommodates the above-mentioned outer needle 21, and a supporting leg 52 which is extended in the axial direction from the above-mentioned outer needle hub supporting portion 51, forming a side face of the protector, and forms an opening at the side face, a locking member 52c is provided at one end side of the above-mentioned supporting leg 52, a locking hole portion 41b1 into which the locking member 52c of the above-mentioned supporting leg 52 is inserted is formed at one end side of the above-mentioned inner needle hub 41, the projection parts 22A and 22B of the above-mentioned outer needle hub 22 are arranged at an opening 53 at the side face of the above-mentioned protector 5, the locking member 52c of the above-mentioned supporting leg 52 is inserted and fitted into the locking hole portion 41b1 of the above-mentioned inner needle hub 41, and the above-mentioned outer needle 21 is accommodated in the above-mentioned outer needle hub supporting portion 51.

According to such a structure, since the opening 53 is formed at the side face of the above-mentioned protector 5, the projection parts 22A and 22B (branch pipe, wings, etc.)

can be provided for the above-mentioned opening 53, and the supporting legs 52 can be fitted to the inner needle hub 41, without interfering with the above-mentioned projection parts 22A and 22B.

That is to say, even in the case where the projection parts, such as the branch pipe and wings, are formed at the outer needle hub 22, the protector 5 can reliably be mounted without enlarging, the outer needle 21 and the inner needle 3 projecting from the tip of the outer needle can be accommodated and protected by the above-mentioned outer needle hub supporting portion 51, and it is possible to prevent them from being displaced and secure safety.

In addition, it is desirable that a plurality of the above-mentioned supporting legs 52 are extended from the above-mentioned outer needle hub supporting portion 51 along the axial direction, and a plurality of the above-mentioned locking hole portions 41b1 are formed at one end side of the above-mentioned inner needle hub 41 corresponding to the locking members 52c provided at one end side of a plurality of the above-mentioned supporting legs 52.

As described above, since it is arranged that each of the locking members 52c provided for a plurality of supporting legs 52 may be fitted into one end side of the inner needle hub 41, the outer needle hub supporting portion 51 can be supported stably.

Further, it is desirable that a plurality of the above-mentioned supporting legs 52 are extended along the axial direction from the above-mentioned outer needle hub supporting portion 51, and the above-mentioned opening 53 is formed between a plurality of the above-mentioned supporting legs 52.

As described above, by providing a plurality of supporting legs 53, a plurality of openings 53 can be circumferentially formed at the side face of the protector 5, and a plurality of projection parts can be provided for these openings 53.

Furthermore, it is desirable that the above-mentioned protector 5 has the elastic component 54 which is compressible in the axial direction, and the above-mentioned elastic component 54 is compressed in a situation where the locking member 52c of the above-mentioned supporting leg 52 is fitted into the locking hole portion 41b1 of the above-mentioned inner needle hub 41, thus biasing the protector 5 in the direction to separate it from the above-mentioned inner needle hub 41.

As described above, provision of the elastic component 54 allows the fit between the protector 5 and the inner needle hub 41 to be more reliable. Further, separation of the protector 5 (removal of protector) from the inner needle hub 41 can easily be performed with the biasing force of the elastic component 54, and it is possible to prevent the outer needle hub from being displaced.

As described above, according to the eighth preferred embodiment in accordance with the present invention, the opening 53 is formed between the supporting legs 52 at the side face of the protector 5, so that the branch pipe 22B of the outer needle hub 22 and the pair of wings 22A can be arranged in the above-mentioned opening 53, and the supporting legs 52 can be fitted to the inner needle hub 41, without interfering with the above-mentioned branch pipe 22B and wings 22A.

That is to say, even if the branch pipe 22B or wings 22A are provided for the outer needle hub 22, the protector 5 can reliably be mounted without enlarging, the outer needle 21 and the inner needle 3 projecting from the tip of the outer needle 21 can be accommodated and protected by the outer needle hub supporting portion 51, and it is possible to prevent them from being displaced and secure safety.

The invention claimed is:

1. A puncture device, comprising:
an outer needle,
an outer needle hub for retaining a base portion of said outer needle,
an inner needle whose tip portion is inserted in said outer needle,
an inner needle hub for retaining a base portion of said inner needle,
an outer pipe fitted inside the inner needle hub so as to be moveable to and fro,
an inner pipe having a gripping means for gripping said outer needle hub, the inner pipe being fitted inside said outer pipe so as to be moveable to and fro,
wherein the gripping means includes
 a plurality of arms formed at said inner pipe for gripping said outer needle hub, and
 an arm opening/closing part that grasps said outer needle hub when said plurality of arms are retracted into the arm opening/closing part and that releases said outer needle hub when said plurality of arms are advanced from the arm opening/closing part, and
 wherein at least said outer pipe is formed of a soft synthetic resin material.

2. A puncture device as claimed in claim 1, wherein said inner pipe is formed of a soft synthetic resin material.

3. A puncture device as claimed in claim 1, wherein said inner needle hub is formed of a soft synthetic resin material.

4. A puncture device as claimed in claim 1, wherein said inner pipe and said inner needle hub are formed of a soft synthetic resin material.

5. A puncture device as claimed in claim 4, wherein said soft synthetic resin material is a synthetic resin whose elongation percentage is 200% or more.

6. A puncture device as claimed in claim 4, wherein said soft synthetic resin material is polypropylene.

7. A puncture device as claimed in claim 1, wherein said soft synthetic resin material is a synthetic resin whose elongation percentage is 200% or more.

8. A puncture device as claimed in claim 1, wherein said soft synthetic resin material is polypropylene.

9. A puncture device as claimed in claim 1,
wherein said inner needle hub is provided with a through hole having a diameter that is smaller than an inner diameter of said inner needle hub,
wherein said outer pipe has a diameter smaller than a diameter of the arm opening/closing part,
wherein said outer pipe is provided with a shaft that is moveable through the through hole of the inner needle hub, and
wherein said shaft passes through the through hole of the inner needle hub when said outer pipe is moved in the inner needle hub.

10. A puncture device as claimed in claim 1,
wherein a relay pipe that extends said outer pipe is provided between said inner needle hub and said outer pipe,
wherein the relay pipe is accommodated in said inner needle hub and accommodates said outer pipe therein,
wherein said inner needle hub is provided with a through hole having a diameter that is smaller than an inner diameter of said inner needle hub, and wherein said relay pipe passes through the through hole of the inner needle hub when said outer pipe is moved in the inner needle hub.

\* \* \* \* \*